US010836788B2

(12) United States Patent
Ge

(10) Patent No.: US 10,836,788 B2
(45) Date of Patent: Nov. 17, 2020

(54) AQUEOUS SUSPENSION COMPOSITIONS, FORMULATIONS, AND WATER DISPERSIBLE DRY COMPOSITIONS COMPRISING 16ALPHA-BROMO-3BETA-HYDROXY-5ALPHA-ANDROSTAN-17-KETONE AND HYDRATES, DERIVATIVES, AND ANALOGS THEREOF

(71) Applicant: SD Chem, Inc., San Diego, CA (US)

(72) Inventor: Yu Ge, San Diego, CA (US)

(73) Assignee: SD Chem, Inc., San Diego, CA (US)

( * ) Notice: Subject to any disclaimer, the term of this patent is extended or adjusted under 35 U.S.C. 154(b) by 0 days.

(21) Appl. No.: 16/267,815

(22) Filed: Feb. 5, 2019

(65) Prior Publication Data
US 2020/0247838 A1    Aug. 6, 2020

(51) Int. Cl.
| | | |
|---|---|---|
| *C07J 1/00* | (2006.01) |
| *A61K 9/00* | (2006.01) |
| *A61K 31/5685* | (2006.01) |
| *A61P 1/00* | (2006.01) |
| *A61P 31/06* | (2006.01) |
| *A61P 37/06* | (2006.01) |
| *A61P 3/10* | (2006.01) |
| *A61P 35/00* | (2006.01) |
| *A61K 9/19* | (2006.01) |
| *A61K 47/34* | (2017.01) |
| *A61K 47/38* | (2006.01) |
| *A61P 11/06* | (2006.01) |

(52) U.S. Cl.
CPC .......... *C07J 1/0011* (2013.01); *A61K 9/0019* (2013.01); *A61K 9/19* (2013.01); *A61K 31/5685* (2013.01); *A61K 47/34* (2013.01); *A61K 47/38* (2013.01); *A61P 1/00* (2018.01); *A61P 3/10* (2018.01); *A61P 11/06* (2018.01); *A61P 31/06* (2018.01); *A61P 35/00* (2018.01); *A61P 37/06* (2018.01)

(58) Field of Classification Search
CPC .......... C07J 1/00; A61K 9/00; A61K 31/5685; A61K 9/19; A61K 47/34; A61K 47/38; A61P 1/00; A61P 31/06; A61P 37/06; A61P 3/10; A61P 35/00; A61P 11/06
See application file for complete search history.

(56) References Cited

U.S. PATENT DOCUMENTS

| | | |
|---|---|---|
| 3,710,795 A | 1/1973 | Higuchi et al. |
| 3,711,606 A | 1/1973 | Herschler |
| 4,542,129 A | 9/1985 | Orentreich |
| 4,898,694 A | 2/1990 | Schwartz et al. |
| 4,978,532 A | 12/1990 | El-Rashidy |
| 5,077,284 A | 12/1991 | Loria et al. |
| 5,206,008 A | 4/1993 | Loria |
| 5,407,684 A | 4/1995 | Loria et al. |
| 5,709,878 A | 1/1998 | Rosenbaum et al. |
| 5,714,481 A | 2/1998 | Schwartz et al. |
| 5,753,237 A | 5/1998 | Daynes et al. |
| 5,804,576 A | 9/1998 | Schwartz et al. |
| 5,824,668 A | 10/1998 | Rubinfeld et al. |
| 5,856,340 A | 1/1999 | Bolonick et al. |
| 5,863,910 A | 1/1999 | Bolonick et al. |
| 5,869,090 A | 2/1999 | Rosenbaum |
| 6,667,299 B1 | 12/2003 | Ahlem et al. |
| 7,396,827 B2 | 7/2008 | Ahlem et al. |
| 7,723,532 B2 | 5/2010 | Frincke et al. |
| 8,106,036 B2 | 1/2012 | Frincke |
| 2002/0032160 A1 | 3/2002 | Nyce |
| 2003/0060425 A1 | 3/2003 | Ahlem et al. |
| 2009/0317477 A1 | 12/2009 | Robinson et al. |
| 2015/0353596 A1 | 12/2015 | Frincke |

FOREIGN PATENT DOCUMENTS

| | | |
|---|---|---|
| RU | 2295534 * | 3/2007 |
| WO | WO 2000056757 A1 | 9/2000 |
| WO | WO 2012/013816 A1 | 2/2012 |

OTHER PUBLICATIONS

Moss, P. et al., "Glossary of class names of organic compounds and reactive intermediates based on structure," Pure &Appl. Chem., 67 (819), 1307-1375 (1995).
Carli, M. et al., "Human TH1 and TH2 cells: functional properties, regulation of development and role in autoimmunity," Autoimmunity, 18 (4), 301-308 (1994).
Ana María Leal-Díaz, M. et al., "Aguamiel concentrate from Agave salmiana and its extracted saponins attenuated obesity and hepatic steatosis and increased Akkermansia muciniphila in C57BL6 mice," Sci. Rep., Nature, 6, 34242 (2016).
Balin, B., et al., "Identification and localization of Chlamydia pneumoniae in the Alzheimer's brain," Med Microbiol Immunol., 187, 23-42 (1998).

(Continued)

*Primary Examiner* — Shirley V Gembeh
(74) *Attorney, Agent, or Firm* — Mei & Mark LLP; Manni Li

(57) ABSTRACT

Unusual and unexpectedly stable aqueous suspension formulation and water dispersible dry composition of Formula I compounds. It causes little or no injection site irritation and has superior properties over non-aqueous formulations. It stimulates autophagy, enhance innate immunity, down-regulates unproductive inflammation and exerts a Th1 immune bias. It demonstrates better efficacy in both in vitro and in vivo models.

Formula I

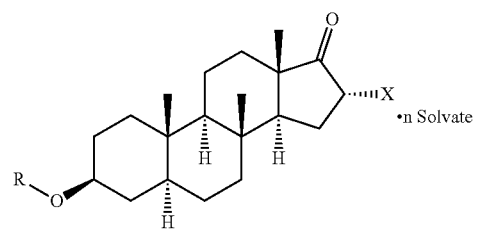

16 Claims, 5 Drawing Sheets

(56) References Cited

OTHER PUBLICATIONS

Black, P. et al., "Serological evidence of infection with Chlamydia pneumoniae is related to the severity of asthma", Eur Respir J., 15(2), 254-9 (2000).
Blanchard, T., et al., "Chlamydia neumoniae and atherosclerosis," Lancet, 341, 825 (1993).
Blasi, F., et al., "Chlamydia pneumoniae infection in acute exacerbations of COPD," Eur. Respir. J., 6, 19-22 (1993).
Borst, J. et al., "CD4+ T cell help in cancer immunology and immunotherapy," Nature Reviews Immunology, 18, 635-647 (2018).
Carrero, J. et al., "Parasiticidal effect of 16α-bromoepiandrosterone (EpiBr) in amoebiasis and cysticercosis, Microbes and Infection," 12 (8-9), 677-82 (2010).
Chesi, M., et al., "Drug response in a genetically engineered mouse model of multiple myeloma is predictive of clinical efficacy," Blood, 120(2), 376-385 (2012).
Chiodini, R., et al., "Possible role of mycobacteria in inflammatory bowel disease. I. An unclassified Mycobacterium species isolated from patients with Crohn's disease," Dig. Dis. Sci., 29, 1073-1079 (1984).
Clerici, M., et al., "TH1→TH2 switch is a critical step in the etiology of HIV infection" Immunol. Today, 14, 107-111 (1993).
Clerici, M., et al., "The Th1-Th2 hypothesis of HIV infection: new insights", Immunol. Today, 15, 575-581 (1994).
Cossu, D., et al., "Association of *Mycobacterium avium* subsp. *paratuberculosis* with Multiple Sclerosis in Sardinian Patients," PLoS ONE 6(4): e18482 (2011).
Deretic, V., "Autophagy in Tuberculosis," Cold Spring Harbor Perspectives in Medicine (2014).
Frincke J. M., et al., "Reduction of Parasite Levels in Patients with Uncomplicated Malaria by Treatment with HE2000," Am. J. Trop. Med. Hyg., 76 (2), 232-6 (2007).
Galeone, C., et al., "Precision Medicine in Targeted Therapies for Severe Asthma: Is There Any Place for (Omics) Technology?," BioMed Research International, Article ID 4617565, 15 pages (2018).
Hernandez-Pando, R., et al., "16a-Bromoepiandrosterone Restores T Helper Cell Type 1 Activity and Accelerates Chemotherapy-Induced Bacterial Clearance in a Model of Progressive Pulmonary Tuberculosis," Journal of Infectious Diseases, 191, 299-306 (2005).
Itzhaki, R., et al., "Microbes and Alzheimer's Disease," J. Alzheimers Dis., 51(4): 979-984 (2016).
Kawano, M., et al., "Autocrine generation and requirement of BSF-2/IL-6 for human multiple myelomas," Nature, 332(6159), 83-85 (1988).
Liang, Y. et al., "Rifampicin inhibits rotenone-induced microglial inflammation via enhancement of autophagy," Neuro Toxicology, 63, 137-45 (2017).
Lord, J., et al., "The systemic immune response to trauma: an overview of pathophysiology and treatment," Lancet, 384(9952), 1455-1465 (2014).
Cheryl Villareal et al., "Persistent Chlamydiae and chronic arthritis," Arthritis Res., 4 (1), 5-9 (2002).
Nakahira, K. et al., "Autophagy proteins regulate innate immune responses by inhibiting the release of mitochondrial DNA mediated by the NALP3 inflammasome," Nat. Immunol., 12(3), 222-30 (2011).
Nicoletti, F. et al., "16alpha-Bromoepiandrosterone (HE2000) limits non-productive inflammation and stimulates immunity in lungs," Clin Exp Immunol., 158(3), 308-16 (2009).
Numazawa, M., et al., "Stereoslective Hydrolysis of 16α-17-Keto Steroids and Long-range Substitution Effects on the Hydrolysis of 16α-Bromo-17-Ketones and 2a-Bromo-3-Ketones," Steroid, 45(5), 403-10 (1985).
Numazawa, M., et al., "Stereospecific Synthesis of 16a-Hydroxy-17-oxo Steroids by Controlled Alkaline Hydrolysis of Corresponding 16-Bromo-17-Ketones and its Reaction Mechanism," J. Org. Chem, 47(21), 4024-4029 (1982).
Raineri et al., Biochemistry 1970 9: 2233-2243.
Reading, C., et al., "Improvement in Immune Parameters and Human Immunodeficiency Virus-1 Viral Response in Individuals Treated with 16alpha-bromoepiandrosterone (HE2000)," Clin. Microbiol. Infect., 12(11), 1082-8 (2006).
Nema, S. et al., "Excipients and their use in injectable products," PDA J. Pharm. Sci. Tech. 1997 51 :166-171.
Sharp, R. et al., "Polymorphisms in Protein Tyrosine Phosphatase Non-receptor Type 2 and 22 (PTPN2/22) Are Linked to Hyper-Proliferative T-Cells and Susceptibility to Mycobacteria in Rheumatoid Arthritis," Front. Cell. Infect. Microbiol., vol. 8, Article 11 (2018).
Shi, Y., et al., "Interplay between innate immunity and Alzheimer disease: APOE and TREM2 in the spotlight," Nature Reviews Immunology, 18, 759-772 (2018).
Shimada, K., et al., "Innate immune responses to Chlamydia pneumoniae infection: Role of TLRs, NLRs, and the Inflammasome," Microbes Infect., 14(14), 1301-1307 (2012).
Sriram, S., et al., "Multiple sclerosis associated with Chlamydia pneumoniae infection of the CNS," Neurology, 50, 571-572 (1998).
Stickney, D., et al., "Safety and Activity of the Immune Modulator HE2000 on the Incidence of Tuberculosis and Other Opportunistic Infections in AIDS Patients," Antimicrob. Agents Chemother, 51 (7), 2639-41 (2007).
Xiong, Y., et al., "Identification of two groups of smoldering multiple myeloma patients who are either high or low producers of interleukin-1," J. Interferon Cytokine Res., 26(2), 83-95 (2006).

\* cited by examiner

AQUEOUS SUSPENSION COMPOSITIONS, FORMULATIONS, AND WATER DISPERSIBLE DRY COMPOSITIONS COMPRISING 16ALPHA-BROMO-3BETA-HYDROXY-5ALPHA-ANDROSTAN-17-KETONE AND HYDRATES, DERIVATIVES, AND ANALOGS THEREOF

FIELD OF INVENTION

The present invention relates to aqueous suspension composition and formulation of the pharmaceutical substance 16alpha-bromo-3beta-hydroxy-5alpha-androstan-17-ketone and the hydrates, solvates, derivatives, and analogs thereof. Furthermore, the present invention also relates to the processes of preparation and use of the compositions and formulations in pharmaceutical and non-pharmaceutical applications, such as immune modulators, containing the pharmaceutical substance.

BACKGROUND OF THE PRESENT INVENTION

16alpha-bromo-3beta-hydroxy-5alpha-androstan-17-ketone (BEA) is a synthetic analog of dehydroepiandrosterone (DHEA) having the following formula:

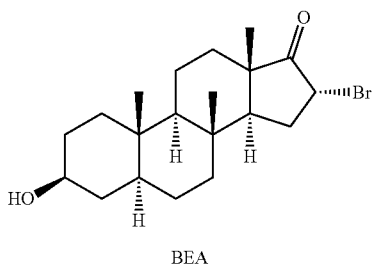

BEA

As an alpha-bromo ketone, BEA is known to be susceptible to nucleophilic attack and the 16alpha-bromine is displaced by nucleophiles. See Numazawa, M., et al., "Stereoselective Hydrolysis of 16alpha-17-Keto Steroids and Long-range Substitution Effects on the Hydrolysis of 16alpha-Bromo-17-Ketones and 2a-Bromo-3-Ketones," Steroid, 45(5), 403-10 (1985). Therefore, BEA is in general not stable chemically.

BEA is also known to go through epimerization at 16-position and lose the chiral purity in the presence of water. See Numazawa, M., et al., "Stereospecific Synthesis of 16alpha-Hydroxy-17-oxo Steroids by Controlled Alkaline Hydrolysis of Corresponding 16-Bromo-17-Ketones and its Reaction Mechanism," J. Org. Chem, 47(21), 4024-4029 (1982).

Since BEA is extremely insoluble in water, the injectable formulations are often made as a non-aqueous solution. Because of BEA's chemical instability and epimerization in the presence of water, non-aqueous solutions have to be extremely dry and the water content generally cannot be greater than 0.1% in order to make it more stable. However, even with such a low water content, solution formulations are still not stable. The sterilization, dividing and packaging of the formulations have to be conducted under low temperature. These formulations have to be stored under low temperature as well. See U.S. Patent Application Publication US2003060425A1 to Ahlem, C., et al. However, even with extremely low water content, the formulations are still not stable as shown in the following Example 2.

The poor stability of BEA makes it not suitable for pharmaceutical use. The compound has to be formulated right before injection. In order to make BEA a viable drug, a new formulation that can stabilize BEA is required.

The non-aqueous BEA injectable formulations are made by dissolving BEA into organic solvents such as polyethylene glycol, propylene glycol, benzyl benzoate, and benzyl alcohol. It has been found that the non-aqueous solution formulations cause severe injection site irritation both in animals and in human, which seriously impacts patient's compliance. The reason for the injection site irritation is due to BEA's poor water solubility. Once the organic BEA solution is in contact with water after injection, BEA will precipitate immediately and form a large piece of solid in tissues and cause the irritation.

The organic solvent is used to make the injectable BEA solution. When the BEA solution is administered, the large amount of organic solvent is injected into the body. The poor tolerance of organic solvent is another source of injection site irritation. In order to eliminate the irritation and toxicity caused by the organic solvents, thus, a water based formulation is desired.

DHEA and other steroids are known to have various applications, e.g., modulating immune responses. See, for examples, U.S. Pat. Nos. 5,869,090, 5,863,910, 5,856,340, 5,824,668, 5,804,576, 5,753,237, 5,714,481, 5,709,878, 5,407,684, 5,206,008, 5,077,284, 4,978,532, 4,898,694, 4,542,129, 3,711,606, and 3,710,795. BEA has been used as an immunoregulatory steroid for the therapy of Human Immunodeficiency Virus (HIV), Tuberculosis (TB), and Malaria by intramuscular or subcutaneous injection and oral mucosal administration.

Stickney, D., et al., "Safety and Activity of the Immune Modulator HE2000 on the Incidence of Tuberculosis and Other Opportunistic Infections in AIDS Patients," Antimicrob. Agents Chemother, 51 (7), 2639-41 (2007) discloses that the incidence of tuberculosis and the infection rate of AIDS patients is reduced by intramuscular injection of preparations containing BEA and excipients such as polyethylene glycol 300, propylene glycol, benzyl benzoate, and benzyl alcohol. However, the results show severe injection site irritations.

Reading, C., et al., "Improvement in Parameters and Human Immunodeficiency Virus-1 Viral Response in Individuals Treated with 16alpha-bromoepiandrosterone (HE2000)," Clin. Microbiol. Infect., 12(11), 1082-8 (2006) discloses use of another BEA formulation for trials in patients with HIV by subcutaneous injection. The formulation is a solution of BEA in PEG200, propylene glycol, benzyl benzoate, and benzyl alcohol. The clinical trials investigate the effects on HIV activity, immune effect, tolerance and safety, and results show that IL-1beta, TNF-alpha, IL-6 and Cox-2 transcripts in BEA groups are significantly reduced while $CD8^+$ is significantly increased. The results of the safety trial show again that BEA causes severe injection site irritation and is poorly tolerated.

Frincke J. M., et al., "Reduction of Parasite Levels in Patients with Uncomplicated Malaria by Treatment with HE2000," Am. J. Trop. Med. Hyg., 76 (2), 232-6 (2007) discloses use of two BEA formulations for trials in patients with malaria by subcutaneous injections and mucosal drug delivery system. The formulation for subcutaneous injections is a solution of BEA in PEG200, propylene glycol, benzyl benzoate, and benzyl alcohol. The formulation for mucosal drug delivery system is a mixture of BEA and excipients such as lactose, crospovidone, mannitol, magnesium stearate, and silica. The clinical trials investigate safety, tolerance, and anti-malaria activity of the BEA preparations. The results prove that the two different preparations show similar anti-malarial response. The safety trial shows that the most frequent adverse event is the high incidence of severe pain at the injection site.

Hernandez-Pando, R., et al., "16a-Bromoepiandrosterone Restores T Helper Cell Type 1 Activity and Accelerates Chemotherapy-Induced Bacterial Clearance in a Model of Progressive Pulmonary Tuberculosis," Journal of Infectious Diseases, 191, 299-306 (2005) discloses that BEA restores Th1 activity in BALB/c mice with pulmonary tuberculosis infected by *Mycobacterium tuberculosis* and inhibition of bacterial proliferation, and increased expression of TNF-alpha, IFN-γ, and iNOS are observed. When given as an adjunct to a conventional chemotherapy (rifampicin, isoniazid, and pyrazinamide), BEA enhances bacterial clearance.

Nicoletti, F. et al., "16alpha-Bromoepiandrosterone (HE2000) limits non-productive inflammation and stimulates immunity in lungs," Clin Exp Immunol., 158(3), 308-16 (2009) discloses that BEA decreases nitric oxide production by lipopolysaccharide (LPS)-stimulated RAW264.7 cells. Treatment with BEA also reduces non-productive inflammation associated with carrageenan-induced pleurisy and LPS-induced lung injury in mice. In the hapten-carrier reporter antigen popliteal lymph node assay, BEA increases absolute numbers of lymphocytes, antigen-presenting cells, hapten-specific immunoglobulin M (IgM) antibody-forming cells and shifts the interferon-gamma (IFN-gamma)/interleukin-4 (IL-4) balance towards IFN-gamma production. In the cystic fibrosis transmembrane conductance regulator (CFTR(−/−)) mouse model of acute *Pseudomonas aeruginosa* infection, treatment with BEA consistently reduces bacterial burden in lungs. All BEA effects are dose-dependent. BEA reduces mortality related to excessive inflammation and opportunistic lung infections in animals and patients.

Carrero, J. et al., "Parasiticidal effect of 16alpha-bromoepiandrosterone (EpiBr) in amoebiasis and cysticercosis, Microbes and Infection," 12 (8-9), 677-82 (2010) discloses the effect of BEA on the tapeworm *Taenia crassiceps* and the protist *Entamoeba histolytica*, both in vivo and in vitro and finds that administration of BEA prior to infection with cysticerci in mice reduces the parasite load by 50% compared with controls. BEA treatment also induces 20% reduction on the development of amoebic liver abscesses in hamsters. In vitro treatment of *T. crassiceps* and *E. histolytica* cultures with BEA reduces reproduction, motility, and viability in a dose- and time-dependent fashion. These results leave open the possibility of assessing the potential of the hormonal analog as a possible anti-parasite drug, including cysticercosis and amoebiasis.

Autophagy is an evolutionary conserved intracellular process that allows cells to remove unwanted molecules, organelles, and microbes. Robust autophagy is especially important to the function of innate phagocytic cells (macrophages and dendritic cells) in their roles as central antigen processing cells and as end-stage effector cells that kill microbes. Macrophages handle *Mycobacterium tuberculosis* and other microbial infections through the autophagy process. Autophagy enzymes guide lipids from the endoplasmic reticulum to surround the microbe, enveloping it in an autophagic vacuole. Lysosomes fuse with it bringing in microbicidal constituents that destroy the bacterium. Information stored in the molecules of the microbe are interpreted by pattern recognition receptors triggering pathways that direct the nucleus to activate appropriate genetic networks to synthesize appropriate signaling cytokine and receptor transcripts. Digested antigens are presented along with appropriate signaling molecules by the MHC apparatus to T cells of the adaptive arm of the immune network thus coordinating an effective global immune response. Effective autophagy and Th1/cell-mediated responses are required to effectively control mycobacterial infections. As a component of the integrated response, properly functioning autophagy is critical in down-regulating inflammation by turning off the NALP3 inflammasome and stopping the release of pro-inflammatory IL-1beta. See Deretic, V., "Autophagy in Tuberculosis," Cold Spring Harbor Perspectives in Medicine (2014).

The end result of compromised autophagy is persistent microbial infection, inappropriate cytokine production, flawed antigen presentation to T-cells of the adaptive immune network, dysregulated immune signaling, and failure to downregulate IL-1beta resulting in chronic damaging inflammatory disease. See, Nakahira, K. et al., "Autophagy proteins regulate innate immune responses by inhibiting the release of mitochondrial DNA mediated by the NALP3 inflammasome," Nat. Immunol., 12(3), 222-30 (2011); Liang, Y. et al., "Rifampicin inhibits rotenone-induced microglial inflammation via enhancement of autophagy," Neuro Toxicology, 63, 137-45 (2017).

Vigorous Th1 (helper Tell 1) response in murine system helps clear infection or slow the progression of an infection. When a subject's immune response is biased to a Th2-type response, it tends to suppress the immune system's capacity to mount a vigorous Th1 response. Insufficient Th1 response may be associated with progression of some infections or other conditions. See Clerici, M., et al., Immunol. Today, 14, 107-111 (1993); Clerici, M., et al., Immunol. Today, 15, 575-581 (1994).

Hormonal control of biological pathways in metazoans involves complex processes in different cell types integrated into functional responses often involving redundant and parallel signaling pathways. 'Pioneer' transcription factors open up large and related genetic networks from covering histones that are further tuned by other transcription factors to select out which genes are eventually transcribed. BEA act similarly to other steroid hormones as pioneer transcription factors to orchestrate a complex immune response. As a results of its ability to stimulate autophagy, BEA stimulates innate immunity, down-regulates unproductive inflammation, exerts a Th1 immune bias and demonstrates activity against viruses, bacteria, protozoa and helminths.

An agent that is able to influence innate immunity and inflammation will have a therapeutic role in trauma, infectious, neoplasia, metabolic, autoimmune, neuro-inflammatory and vascular disease processes. Therefore, *Mycobacterium tuberculosis* (MTB), non-tuberculosis mycobacteria diseases, all viral, bacteria, protozoal, fungal and helminthic diseases involving immunity and inflammation, bacterial pneumonias involving respirators are clear targets for BEA.

BEA exerts beneficial effects on a spectrum of diseases involving seemingly different disease processes due to its action on fundamental biological signaling pathways involving autophagy and inter-connected intracellular signaling pathways. BEA's ability to stimulate innate immunity while re-establishing control of dysregulated, unproductive inflammation is key to its efficacy. Many acute and chronic infectious, neoplastic and idiopathic chronic inflammatory diseases are associated with dysregulated immune signaling associated with compromised autophagy and dysregulated signaling pathways, both intracellular and extracellular. Acting as a hormone, BEA elicits responses in different cell types throughout the host resulting in restoration of 'dynamic homeostasis' of the immune network. The term implies that BEA restores the ability of the immune system to function correctly as evidenced by BEA's ability to enhance innate immunity, down-regulate unproductive inflammation, promote Th1 cell mediated immune processes and more effectively respond to threats from microbial PAMPS (pathogen associated molecular patterns) and neoplastic DAMPS (danger associated molecular patterns) interpreted through PRR (pattern recognition receptors) pathways. BEA's influence on dendritic cells and macrophages as professional antigen presenting cells influencing downstream signaling of the adaptive immune system is central to its global systemic effect on restoring immune dynamic homeostasis.

*Mycobacterium avium* ss. paratuberculosis (MAP) is an acid-fast staining small rod-shaped bacterium which has been associated with Crohn's disease, rheumatoid arthritis, Blau syndrome, type 1 diabetes, Hashimoto thyroiditis, multiple sclerosis, and Sarcoidosis. The bacterium also causes Johne's disease in cattle and other ruminants. The fact that BEA can inhibit bacterial proliferation and increase expression of TNF-alpha, IFN-gamma, and iNOS of mice infected with MTB (See R. Hernandez-Pando et al. (2005)) indicates that BEA may be used to treat not only MTB, but also Crohn's disease, rheumatoid arthritis, Blau syndrome, type 1 diabetes, Hashimoto thyroiditis, multiple sclerosis, Sarcoidosis, and Johne's disease.

Extensive studies have been conducted to determine whether MAP is involved in the pathogenesis of Crohn's disease (CD), a chronic inflammatory bowel disease that occurs in humans. The isolation of MAP from patients with CD during the 1980s provided the first direct evidence for a potential role of MAP in CD pathogenesis. See Chiodini, R., et al., "Possible role of mycobacteria in inflammatory bowel disease. I. An unclassified *Mycobacterium* species isolated from patients with Crohn's disease," Dig. Dis. Sci., 29, 1073-1079 (1984). The mechanisms leading to breakdown in protective immunity in CD patients are expected to be similar to those associated with a breakdown in protective immunity to MTB. Since BEA is effective in treating MTB, it's expected to be effective in treating CD.

Rheumatoid arthritis (RA) has been linked to CD because of their shared genetic predisposition, chronic inflammation, and treatment with similar biologics. A recent study discovered the link between the two: MAP. (Sharp, R. et al., "Polymorphisms in Protein Tyrosine Phosphatase Non-receptor Type 2 and 22 (PTPN2/22) Are Linked to Hyper-Proliferative T-Cells and Susceptibility to Mycobacteria in Rheumatoid Arthritis," Front. Cell. Infect. Microbiol., Volume 8, Article 11 (2018)). Because RA and CD share the same cause, and are treated with the same drugs, it's reasonable to predict that a drug that can effectively treat CD by inhibiting MAP, should also be effective against RA. Since BEA is effective in an animal model for CD, it should be effective in treating RA.

Many studies have shown that multiple sclerosis is associated with MAP infection. See Cossu, D., et al., "Association of *Mycobacterium avium* subsp. paratuberculosis with Multiple Sclerosis in Sardinian Patients," PLoS ONE 6(4): e18482 (2011). BEA has been successfully used in treating *Mycobacterium tuberculosis*, which is associated with MAP as well. See Stickney et al. (2007). Therefore, BEA may be used to treat multiple sclerosis through the same mechanism as tuberculosis. Type 1 diabetes mellitus (T1DM) is a multifactorial autoimmune disease in which the insulin producing beta cell population is destroyed by the infiltrated T lymphocytes. Even though the exact cause of T1DM is yet to be ascertained, varying degree of genetic susceptibility and environmental factors have been linked to the disease progress and outcome. With the increasing recognition of the link between MAP and Crohn's disease, it has been postulated that MAP is an occult antigen which besides Crohn's could as well be thought to trigger T1DM. Epitope homologies between mycobacterial proteins (Hsp65) and pancreatic glutamic acid decarboxylase (GAD 65) and infant nutrition studies implicate MAP as one of the triggers for T1DM. PCR and ELISA analyses in diabetic patients from Sardinia suggest that MAP acts as a possible trigger for T1DM. Given BEA's effectiveness against *Mycobacterium tuberculosis*, it's conceivable to use BEA formulation to treat T1DM.

*Chlamydia* are Gram-negative, obligate intracellular pathogens and symbionts of diverse organisms, ranging from humans to amoebae. *Chlamydia pneumoniae* is an obligate intracellular bacterium that infects the respiratory tract of many vertebrates, including humans. *Chlamydia pneumoniae* infection causes both asymptomatic and acute pneumonia and bronchitis, and has been associated with the development of and or exacerbation of chronic respiratory diseases like obstructive pulmonary disease (COPD) and asthma, and pathogenesis of infection has been associated with diverse diseases such as atherosclerosis (Blanchard, T., et al., "*Chlamydia* neumoniae and atherosclerosis," Lancet, 341, 825 (1993)), Alzheimer's disease (Balin, B., et al., "Identification and localization of *Chlamydia pneumoniae* in the Alzheimer's brain," Med Microbiol Immunol., 187, 23-42 (1998)), inflammatory arthritis (Cheryl, V. et al., "Persistent Chlamydiae and chronic arthritis," Arthritis Res., 4 (1), 5-9 (2002)), multiple sclerosis (Sriram, S., et al., "Multiple sclerosis associated with *Chlamydia pneumoniae* infection of the CNS," Neurology, 50, 571-572 (1998)), asthma (Galeone, C., et al., "Precision Medicine in Targeted Therapies for Severe Asthma: Is There Any Place for (Omics) Technology?," BioMed Research International, Article ID 4617565, 15 pages (2018)), and chronic obstructive pulmonary disease (COPD) (Blasi, F., et al., "*Chlamydia pneumoniae* infection in acute exacerbations of COPD," Eur. Respir. J., 6, 19-22 (1993)). There is no effective vaccine available, and antibiotics can only be used for a short term. Improving the innate immunity is essential to fight *Chlamydia*. See Shimada, K., et al., "Innate immune responses to *Chlamydia pneumoniae* infection: Role of TLRs, NLRs, and the Inflammasome," Microbes Infect., 14(14), 1301-1307 (2012). BEA may stimulate the innate immunity and enhance the autophagy. Enhanced autophagy may help involved macrophages clear the infection. Therefore, BEA may be used to treat *Chlamydia*, as demonstrated by its effectiveness in treating malaria.

In recent studies, Alzheimer's Disease has been linked to microbe infections, such as herpes simplex virus type 1 (HSV1), *Chlamydia pneumoniae*, and several types of spirochaete. (Itzhaki, R., et al., "Microbes and Alzheimer's Disease," J. Alzheimers Dis., 51(4): 979-984 (2016)). Chronic glial activation is a prominent feature accompanying pathological protein accumulation in the Alzheimer disease brain. Prolonged neuroinflammation may induce neuronal injury and death via multiple ways. Innate immunity has not only a direct effect on neuronal viability, it also affects amyloid-beta and tau pathology build-up, which in turn may influence neurodegeneration. Therefore, innate immunity is an indispensable component in Alzheimer disease pathogenesis and may constitute a driving force for disease progression. Boosting immune activity in the brain to increase waste clearance under homeostatic or pathological status without damaging neurons may be an alternative strategy to treat Alzheimer disease. See Shi, Y., et al., "Interplay between innate immunity and Alzheimer disease: APOE and TREM2 in the spotlight," Nature Reviews Immunology, 18, 759-772 (2018). BEA has the ability to stimulate innate immunity while re-establishing control of dysregulated and unproductive inflammation in both human and animals, thus, it may be used to treat Alzheimer disease by controlling the chronic inflammation.

Metabolic syndrome is a cluster of conditions—increased blood pressure, high blood sugar, excess body fat around the waist, and abnormal cholesterol or triglyceride levels—that occur together, increasing your risk of heart disease, stroke, and diabetes. *Chlamydia pneumoniae* is also being linked to T2DM.

Blasi, F., et al. discloses in a study involving 142 COPD patients that COPD is at least partially associated to *Chlamydia pneumoniae*. BEA's ability to stimulate innate immunity while re-establishing control of dysregulated and unproductive inflammation in both human and animals suggests that it may be used to treat COPD.

Asthma is defined as a chronic inflammatory disease of the airways. It is one of the most common chronic diseases in the world. Even with maximal medical therapy, many patients with asthma do not achieve adequate asthma control resulting in a need for additional anti-asthmatic drugs. The underlying physiological and immunological processes are not fully understood. Black, P. et al, "Serological evidence of infection with *Chlamydia pneumoniae* is related to the severity of asthma", Eur Respir J., 15(2), 254-9 (2000) discloses that *Chlamydia pneumoniae* infection is clearly related to atypical pneumonia, asthma, and possibly ischemic heart disease. Therapeutic use of BEA may decrease airways inflammation in asthma, due to its efficient activation of Th-1 response that is antagonist to the Th-2 cytokine pattern which regulate the allergic reactions.

Traumatic processes involve early inflammation and may result in post 'cytokine storm' immune deficiency. Trauma evokes a systemic reaction that includes an acute, non-specific, immune response associated, paradoxically, with reduced resistance to infection. Treatments that aim to augment the body's immunity against infection significantly reduces infection and mortality. See Lord, J., et al., "The systemic immune response to trauma: an overview of pathophysiology and treatment," Lancet, 384(9952), 1455-1465 (2014). The ability of BEA to restore immune homeostasis would make it effective in treating trauma.

Neoplastic diseases that involve relative immune deficiencies are also targets for BEA. A long held hypothesis supported by ample data suggests that some, if not most, idiopathic chronic inflammatory diseases currently labeled as autoimmune diseases are in fact caused by occult infectious agents. The ability of BEA to down-regulate damaging inflammation and not further compromise immunity offers an improvement on current immune suppressive therapies. Immunotherapy is rapidly becoming a standard treatment modality in cancer. CD8$^+$ cytotoxic T lymphocytes (CTLs) are the preferred tool to target tumors, as they detect intracellular antigens that are presented by MHC class I molecules expressed by all tumor cell types. CD4$^+$ T cells are also required for efficacious antitumor immunity. Maximizing CD4$^+$ T cell help can improve outcomes in cancer immunotherapy strategies. See Borst, J. et al., "CD4$^+$ T cell help in cancer immunology and immunotherapy," Nature Reviews Immunology, 18, 635-647 (2018). BEA has been proven in the human clinical trials that it increases CD8$^+$ level in patients. (Stickney D. et al. (2007)). Therefore, BEA can be used as cancer immunotherapy agent.

Multiple myeloma is a universally fatal B-cell malignancy characterized by the progressive accumulation of monoclonal plasma cells. Interleukin 6 (IL-6) has been shown to be a central growth factor for myeloma cells. See Kawano, M., et al., "Autocrine generation and requirement of BSF-2/IL-6 for human multiple myelomas," Nature, 332(6159), 83-85 (1988). Although many cytokines can stimulate IL-6 production, in myeloma interleukin 1 (IL-1) beta appears to be one of the major cytokines responsible for the paracrine production of IL-6 by marrow stromal cells. See Xiong, Y., et al., "Identification of two groups of smoldering multiple myeloma patients who are either high or low producers of interleukin-1," J. Interferon Cytokine Res., 26(2), 83-95 (2006). A mouse model of multiple myeloma based on M-Spike, or M-protein, has been shown in clinical trials to a predictor of effectiveness of an anti-multiple myeloma drug. See Chesi, M., et al., "Drug response in a genetically engineered mouse model of multiple myeloma is predictive of clinical efficacy," Blood, 120(2), 376-385 (2012). The ability of BEA to restore Th1 and reduce IL-1beta and IL-6 makes it a potential drug to treat multiple myeloma.

BEA enhances the ability of neutrophils and macrophages to kill pathogenic microbes, modulates the excessive inflammatory response and ameliorates the ensuing immune deficiency state. Therefore, it can be used to treat acute infectious/inflammatory conditions such as pneumonias, sepsis, and pancreatitis.

Many animal models used during the development of BEA had shown that BEA is effective in treating animal diseases. Therefore, all the animal diseases that are equivalent to human diseases that BEA treats can be treated by BEA as well.

SUMMARY OF THE PRESENT INVENTION

To minimize the rapid precipitation and to prevent the formation of a large piece of solid, and therefore reduce or eliminate the injection site irritation in a pharmaceutical formulation, the present invention provides a suspension made out of small particles of BEA. In the present invention, an aqueous suspension formulation of BEA is designed to solve the problems with current BEA formulations: poor stability, severer injection site irritation, and difficult to manufacture, store, and use.

Contrary to the common chemical knowledge and those disclosed in the publications, the present invention shows that BEA is unusually stable in water as a solid in the composition of the present invention. It's believed that the unusual stability of solid BEA in the composition of the present invention is due to its extremely poor solubility in water. The poor solubility prevents the free water molecule from entering into BEA particles and protects BEA from hydrolysis, epimerization, and other degradation. By making a water suspension formulation of solid BEA, the present invention solves the issue of stability of the existing formulation. A side by side stability studies between the formulation of the present invention and formulations published in the literature demonstrate that the present invention formulation is far more stable than the known formulation.

By using fine particles of BEA in the formulation of the present invention, it prevents the rapid and unorderly precipitation of BEA and form a big piece of solid in tissue. The process, together with the elimination of the organic solvents, dramatically improved the injection site irritation. An extensive study on injection site irritation prove the present invention formulation of BEA is far superior to the known formulation.

The present invention provides compositions, formulations, and methods to accomplish the following objects.

The first object of the present invention is to provide new formulation and composition that are suitable for therapeutic and other applications, such as immune modulators. The new formulation and composition of the present invention include BEA hemihydrate compositions that comprise BEA hemihydrate and methods to make and use the same.

The second object of the present invention is to provide aqueous suspension compositions and formulations that comprise a Formula I compound(s) and use water as solvent.

The third object of the present invention is to provide water dispersible dry compositions that can be used as intermediates to prepare human pharmaceutical and veterinary formulations containing a Formula I compound(s).

The fourth object of the present invention is to provide intermittent dosing methods to deliver a Formula I compound to a subject to enhance Th1 immune responses.

The fifth object of the present invention is to provide methods to modulate innate immunity or to enhance Th1 immune responses in a subject by administering to the subject formulations containing a Formula I compound(s) such as BEA.

The sixth object of the present invention is to provide methods to inhibit pathogen, e.g., viral, replication in a subject by administering to the subject formulations containing a Formula I compound(s) such as BEA. The present invention provides formulations useful to ameliorate one or more symptoms of a pathological condition associated with immune suppression or with deficient Th1 immune responses.

The seventh object of the present invention is to provide methods to make and use compositions and formulations comprising a Formula I compound(s).

The present invention provides compositions and formulations that include BEA and one or more excipients suitable for human pharmaceutical use or for veterinary use.

The present invention also provides aqueous suspension formulations with BEA and one or more excipients for parenteral or aerosol administration.

The present invention further provides water dispersible dry compositions of BEA and one or more excipients for parenteral or aerosol administration.

The present invention further provides a method to make aqueous BEA suspension.

The present invention further provides a method to make water dispersible dry compositions of BEA and one or more excipients.

The compositions of the present invention comprise a compound of Formula I, including hydrates and solvates, in amorphous, crystal, co-crystal, polymorph, co-crystal polymorph forms, and one or more excipients, wherein the compound has the following structure:

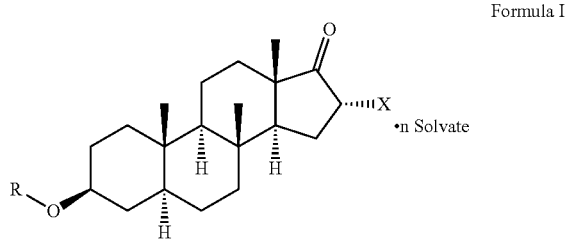

Formula I wherein n is 0 to 4;

the solvate is $H_2O$, $C_{1-4}$—OH, HO—$C_{1-4}$—OH, $C_{1-4}$—COOH, $C_{1-4}$—COO$C_{1-4}$, tetrahydrofuran, 1,4-dioxane, $(CH_3)_2O$, $(C_2H_5)_2O$, $HC(O)N(CH_3)_2$, or $(CH_3)_2SO$;

X is Cl, Br, or I;

R is —H, —Si—$(C_{1-6}$ alkyl)3, an ester, a thioester, a phosphoester, a phosphothioester, a phosphonoester, a phosphiniester, a sulfite ester, a sulfate ester, an amide, an amino acid, a peptide, an ether, a thioether, an acyl group, a thioacyl group, a carbonate, a carbamate, a thiocarbonate, an optionally substituted alkyl group, an optionally substituted alkenyl group, an optionally substituted alkynyl group, an optionally substituted aryl moiety, an optionally substituted heteroaryl moiety, an optionally substituted monosaccharide, an optionally substituted oligosaccharide, a nucleoside, a nucleotide, an oligonucleotide, or a polymer.

The present invention further provides a composition comprising the compound of Formula I and water. The compound of Formula I exists in the water in a form of particles, and the compound of Formula I is as particles in an aqueous suspension in the water. Content of the water is at least 10% w/w in the composition, may be 30% w/w or more in the composition. Preferably, the content of water may be 65% w/w or more, more preferably, the content of water may be 70% w/w or more, and most preferably, the content of water may be 80% w/w or more, and the content of water may reach to 90% w/w or more and the composition of the present invention still maintain the stability of the compound of Formula I therein.

Further, the present invention provides a water dispersible dry composition, that is, a lyophilized composition, that is prepared by freeze-drying or lyophilization of the composition in the water. When the water dispersible dry composition is added with water for use, the compound of Formula I in the composition with water remains stable.

In the composition of the present invention, preferably, the size of the particles of compound of Formula I is in a range of 0.01 μm to 15 μm.

The composition of the present invention may further comprise a surfactant, a suspending agent, and a pharmaceutical excipient.

The surfactant of the present invention may be a poloxamer, polysorbate, polyoxyethylated castor oil polyoxyethylene hydrogenated castor oil, polyethylene glycol (PEG)-8-octylic acid/decanoic acid and polyethylene glycol (PEG) hydroxy stearic acid ester, egg yolk lecithin, soybean lecithin, sodium oleate, bile salt, or a mixture thereof.

The suspending agent of the present invention is cellulose derivatives such as methylcellulose, hydroxyethylcellulose, carboxymethylcellulose, sodium carboxymethylcellulose, microcrystalline cellulose), polyethylene glycol (PEG), polyvinylpyrrolidone (PVP), gelatin, alginates, acacia, tragacanth, xanthan gum, bentonite, carbomer, carrageenan, or a mixture thereof.

The pharmaceutical excipient is water for injection, a pH regulator, an osmotic pressure regulator, a freeze-drying protective additive, a sequestering agent, an antioxidant, a preservative, a medicinal ingredient, or a mixture thereof. When the pharmaceutical excipient is a preservative, it may be methanol, ethanol, n-propanol, isopropanol, n-butanol, 2-butanol, t-butanol, Vitamin C, sodium bisulfite, sodium thiosulfate, sodium metabisulfite, L-cysteine, an amino acid, or a combination thereof.

The composition of the present invention may be an injectable suspension comprising 0.3-25% (w/v) of the compound, 0.01-5% (w/v) of the surfactant, 0.01-3% (w/v)

of the suspending agent, and the osmotic pressure regulator. Preferably, the osmotic pressure regulator is sodium chloride or dextrose.

The composition of the present invention may be a lyophilized formulation comprising the compound of Formula I, a surfactant, a suspending agent, and at least one lyophilization protectant, and the amount of the compound is at 3 mg to 500 mg, a ratio of the compound to the surfactant is 1:50-500:1, and a ratio of the compound to the suspending agent is 0.1:10-500:1.

In the composition of the present invention, the solvate may be water; R may be a hydrogen (H); and X may be a bromine (Br). In one embodiment of the composition of the present invention, the solvate is water, R is a hydrogen, X is a bromine, n is 0.5, and the compound is 16alpha-bromo-3beta-hydroxy-5alpha-androstan-17-ketone hemihydrate having a structure:

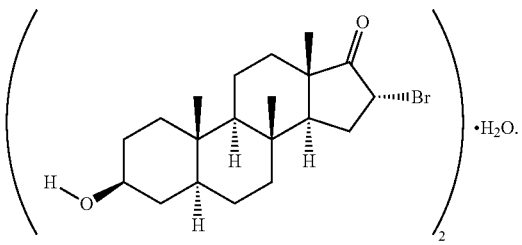

The present invention further provides a method for using the composition comprising the step of administering to a subject in need of a treatment by a parenteral, oral, or aerosol route of administration of the composition.

The present invention further provides a method for using the composition comprising administering to a subject in need of a treatment a therapeutically effective amount of the composition, wherein the treatment is for stimulating autophagy and innate immunity, regulating unproductive inflammation, biasing the immune response towards a Th1 response (IFN-gamma, cellular immune pathways) or a Th2 response, pathological condition (such as a viral or parasite infection), or a combination thereof in the subject. Particularly, the treatment is for infection or dysregulated inflammation, such as trauma, infections (viral, bacterial, protozoa, fungal and helminths), neoplasia, metabolic, autoimmune, or neuro-inflammatory and inflammatory vascular disorders; or *Mycobacterium tuberculosis* and non-tuberculosis mycobacteria, MAP infection, Chlamydial infections, bacterial pneumonias, Inflammatory Bowel Disease (Crohn's and Ulcerative Colitis), multiple myeloma, asthma, metabolic syndrome, type 2 diabetes, type 1 diabetes, obstructive pulmonary disease, trauma, multiple sclerosis, Alzheimer disease, Cardiac sarcoidosis, Rheumatoid Arthritis, or non-alcoholic fatty liver disease.

The present invention further provides a Formula I compound and one or more excipients suitable for human pharmaceutical use or for veterinary use. One embodiment of the present invention includes aqueous suspension formulations with a Formula I compound and one or more excipients for parenteral or aerosol administration. Another embodiment of the present invention provides water dispersible dry compositions of a Formula I compound and one or more excipients for parenteral or aerosol administration. Yet another related embodiment of the present invention provides a method to make aqueous a Formula I compound suspension. Yet another embodiment of the present invention provides a method to make water dispersible dry compositions of a Formula I compound and one or more excipients.

BRIEF DESCRIPTION OF THE DRAWINGS

FIG. 4(a) to 4(d) show the experimental results in Example 10 of the present invention, among which, FIG. 4(a) shows the OGTT results for Estreptozotocin induced type-2 diabetes mellitus (DM2) mice treated with F1 formulation; FIG. 4(b) shows the OGTT results for Estreptozotocin induced type-2 diabetes mellitus (DM2) mice treated with F2 formulation. FIG. 4(c) is the AUC (area under the curve) of blood glucose of OGTT; and FIG. 4(d) is the normal glucose levels of DM2 mice treated with F1 and F2 compared with treated with vehicle.

DETAILED DESCRIPTION OF THE PRESENT INVENTION

Figure 1:
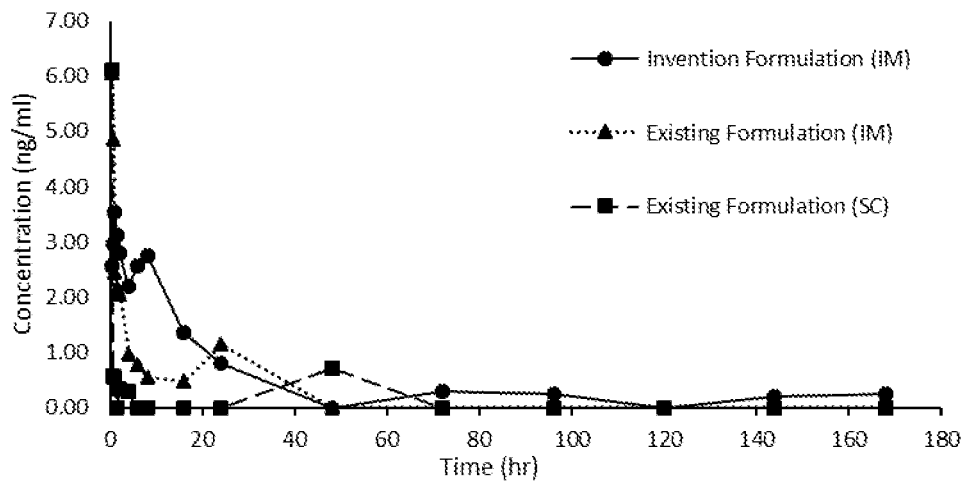
FIG. 1 is a diagram showing the BEA blood concentrations over time as processed and analyzed by LC-MS/MS in Example 6 of the present invention.

As used herein and unless otherwise stated or implied by context, the following terms have the meanings defined here.

A "formulation" or "invention formulation" means an invention composition that one can administer parenterally or aerosolly to a human or animal without further manipulations that change the ingredients or the ingredient proportions that are present. Formulations are suitable for human or veterinary applications.

An "invention composition" is a composition that is an intermediate one can use to make the invention formulations, i.e., a change(s) in an ingredient(s) or its amount(s) is needed to make a formulation. Thus, invention compositions include compositions where further processing is required before it is a formulation, e.g., mixing or addition of a desired amount of an ingredient.

An "excipient" means a component or an ingredient that is acceptable in the sense of being compatible with the other ingredients of invention compositions or formulations and not overly deleterious to the patient or animal to which the formulation is to be administered. As used here, "excipients" include liquids, such as benzyl benzoate, cottonseed oil, N,N-dimethylacetamide, a $C_{2-12}$ alcohol (e.g., ethanol), glycerol, peanut oil, a polyethylene glycol ("PEG"), vitamin E, poppyseed oil, propylene glycol, safflower oil, sesame oil, soybean oil, and vegetable oil. Excipients comprise one or more components typically used in the pharmaceutical formulation arts, e.g., fillers, binders, disintegrants, and lubricants.

A "subject" means a human or animal. Usually the animal is a vertebrate such as a primate, rodent, domestic animal, or game animal. Primates include chimpanzees, cynomologous monkeys, spider monkeys, and macaques, e.g., Rhesus. Rodents include mice, rats, woodchucks, ferrets, rabbits, and hamsters. Domestic and game animals include cows, horses, pigs, deer, bison, buffalo, felines, e.g., domestic cat, canines, e.g., dog, avians, e.g., chicken, emu, ostrich, and fish, e.g., trout, catfish, and salmon. Subject includes any subset of the foregoing, e.g., all of the above, but excluding one or more groups or species such as humans, primates, or rodents.

Expressions that refer to "a Formula I compound(s)" or "a Formula I compound" mean invention compositions or formulations where one or more than one Formula I compound is present, typically 1, 2, 3 or 4, usually 1.

"Alkyl" as used here means linked normal, secondary, tertiary, or cyclic carbon atoms, i.e., linear, branched, or cyclic. The number of carbon atoms in an alkyl group or moiety is 1 to about 20, unless otherwise specified, e.g., $C_{1-8}$ alkyl means an alkyl moiety containing 1, 2, 3, 4, 5, 6, 7, or 8 carbon atoms. Examples include methyl, ethyl, 1-propyl (n-propyl), 2-propyl(i-propyl, —CH(CH$_3$)$_2$), 1-butyl(n-butyl), 2-methyl-1-propyl(i-butyl, —CH$_2$CH(CH$_3$)$_2$), 2-butyl (s-butyl, —CH(CH$_3$)CH$_2$CH$_3$), 2-methyl-2-propyl(t-butyl, —C(CH$_3$)$_3$), 1-pentyl(n-pentyl), 2-pentyl(—CH(CH$_3$)CH$_2$CH$_2$CH$_3$), 3-pentyl(—CH(CH$_2$CH$_3$)$_2$), 2-methyl-2-butyl(—C(CH$_3$)$_2$CH$_2$CH$_3$), 3-methyl-2-butyl(—CH(CH$_3$)CH (CH$_3$)$_2$), 3-methyl-1-butyl(—CH$_2$CH$_2$CH(CH$_3$)$_2$), 2-methyl-1-butyl(—CH$_2$CH(CH$_3$)CH$_2$CH$_3$), 1-hexyl, 2-hexyl(—CH(CH$_3$)CH$_2$CH$_2$CH$_2$CH$_3$), 3-hexyl(—CH$_3$) (CH$_2$CH$_2$CH$_3$)), 2-methyl-2-pentyl(—C(CH$_3$)$_2$ CH$_2$CH$_2$CH$_3$), 3-methyl-2-pentyl(—CH(CH$_3$)CH(CH$_3$) CH$_2$CH$_3$), 4-methyl-2-pentyl(—CH(CH$_3$)CH$_2$CH(CH$_3$)$_2$) 3-methyl-3-pentyl(—C(CH$_3$)(CH$_2$CH$_3$)$_2$), 2-methyl-3-pentyl(—CH(CH$_2$CH$_3$)CH(CH$_3$)$_2$), 2,3-dimethyl-2-butyl(—C (CH$_3$)$_2$CH(CH$_3$)$_2$), 3,3-dimethyl-2-butyl(—CH(CH$_3$)C (CH$_3$)$_3$), cyclopropyl, cyclobutyl, cyclopentyl, and cyclohexyl.

"Alkenyl" means linked normal, secondary, tertiary, or cyclic carbon atoms where one or more double bonds (e.g., —CH=CH—) are present, typically 1, 2, or 3, usually 1 or 2. The number of carbon atoms in an alkenyl group or moiety is 2 to about 20, unless otherwise specified, e.g., $C_{1-8}$ alkenyl means an alkenyl moiety containing 1, 2, 3, 4, 5, 6, 7, or 8 carbon atoms.

"Alkynyl" means linked normal, secondary, tertiary, or cyclic carbon atoms where one or more triple bonds (—C≡C—) are present, typically 1, 2, or 3, usually 1. The number of carbon atoms in an alkynyl group or moiety is 2 to about 20, unless otherwise specified, e.g., $C_{1-8}$ alkynyl means an alkynyl moiety containing 1, 2, 3, 4, 5, 6, 7, or 8 carbon atoms.

"Aryl" means phenyl or naphthyl.

"Substituted alkyl", "substituted alkenyl" and "substituted alkynyl" mean an alkyl, alkenyl, or alkynyl group that has a substituent(s) linked to a carbon atom or substituent(s) that interrupt a carbon atom chain. Substituents include ethers (—O—), ketones (—C(O)—), —OR$^{PR}$, —C(O) OR$^{PR}$, —C(O)O—, —C(S)OR$^{PR}$, —C(S)O—, —OC(O)—, —C(O)H, —OCH$_2$—, —OCH$_2$CH$_2$—, —OCH$_2$O—, —OCH$_2$CH$_2$O—, —NR$^{PR}$—, —N(R$^{PR}$)$_2$, —NHR$^{PR}$, —NHC(O)—, —CH$_2$—NR$^{PR}$—, —CH$_2$—NHR$^{PR}$, —CH$_2$—NHC(O)—, —C(O)NH—, —C(O)NHR$^{PR}$, —OC (O)NR$^{PR}$, —OC(O)NHR$^{PR}$, —NRPRC(O)NR$^{PR}$, —NR$^{PR}$C (O)NHR$^{PR}$, —NR$^{PR}$CH$_2$—, —NR$^{PR}$CH$_2$CH$_2$—, —S—, —SR$^{PR}$, —S(O)—, —S(O)(O)—, —S(O)OR$^{PR}$, S(O)H, —CN, —NO2, halogen, and combinations of these moieties where R$^{PR}$ independently is hydrogen, a protecting group or both R$^{PR}$ together are a protecting group. Substituents are independently chosen when more than one is present. Alkenyl and alkynyl groups that comprise a substituent(s), are typically substituted at a carbon that is one or more methylene moiety removed from the double bond, e.g., separated at least by one, two or more —CH$_2$— moieties. R$^{PR}$ independently is hydrogen, a protecting group or both R$^{PR}$ together are a protecting group.

"Heterocycle" or "heterocyclic" includes by way of example and not limitation the heterocycles described in Moss, P. et al, "GLOSSARY OF CLASS NAMES OF ORGANIC COMPOUNDS AND REACTIVE INTERMEDIATES BASED ON STRUCTURE," Pure & Appl. Chem., 67 (819), 1307-1375 (1995), which are incorporated herein by reference.

Examples of heterocycles include by way of example and not limitation pyridyl, thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2dithiazinyl, thienyl, thianthrenyl, pyranyl, isobenzofuranyl, chromenyl, xanthenyl, phenoxathiinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, beta-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

"Protecting group" means a moiety that prevents the atom to which it is linked from participating in unwanted reactions. For example, for —OR$^{PR}$, R$^{PR}$ may be hydrogen or a protecting group for the oxygen atom found in a hydroxyl, while for —C(O)—OR$^{PR}$, R$^{PR}$ may be hydrogen or a carboxyl protecting group, for —SR$^{PR}$, R$^{PR}$ may be hydrogen or a protecting group for sulfur in thiols for instance, and for —NHR$^{PR}$ or —N(R$^{PR}$)$_2$—, R$^{PR}$ may be hydrogen or a nitrogen atom protecting group for primary or secondary amines. Hydroxyl, amine and other reactive groups are found in Formula I compounds at, e.g., R$^1$. These groups may require protection against reactions taking place elsewhere in the molecule. The protecting groups for oxygen, sulfur or nitrogen atoms are usually used to prevent unwanted reactions with electrophilic compounds, such as acylating used, e.g., in steroid chemistry.

"Ester" means a moiety that comprises a —C(O)—O— structure. Typically, esters as used here comprise an organic moiety containing about 1-50 carbon atoms (e.g., about 2-20 carbon atoms) and 0 to about 10 independently selected heteroatoms (e.g., O, S, N, P, Si), where the organic moiety is bonded to a Formula I steroid nucleus at, e.g., R$^1$ through the —C(O)—O— structure, e.g., organic moiety-C(O)—O-steroid. The organic moiety usually comprises one or more of any of the organic groups described above, e.g., $C_{1-20}$ alkyl moieties, $C_{2-20}$ alkenyl moieties, $C_{2-20}$ alkynyl moieties, aryl moieties, $C_{2-9}$ heterocycles or substituted derivatives of any of these, e.g., comprising 1, 2, 3, 4 or more substituents, where each substituent is independently chosen. Typical substitutions for hydrogen or carbon atoms in these organic groups include 1, 2, 3, 4 or more, usually 1, 2, or 3-O—, —S—, —NR$^{PR}$— (including —NH—), —C(O)—, =O, =S, —N(R$^{PR}$)$_2$ (including —NH$_2$), —C(O)OR$^{PR}$ (including —C(O)OH), —OC(O)R$^{PR}$ (including —O—C(O)—H), —OR$^{PR}$ (including —OH), —SR$^{PR}$ (including —SH), —NO$_2$, —CN, —NHC(O)—, —C(O)NH—, —OC(O)—, —C(O)O—, —O-A8, —S-A8, —C(O)-A8, —OC(O)-A8, —C(O)O-A8, =N—, —N=, =N—OH, —OPO$_3$(R$^{PR}$)$_2$, —OSO$_3$H$_2$ or halogen moieties or atoms, where each R$^{PR}$ is —H, an independently selected protecting group or both R$^{PR}$ together comprise a protecting group, and A8 is C$_{1-8}$ alkyl, C$_{2-8}$ alkenyl, C$_{2-8}$ alkynyl, C$_{1-4}$ alkyl-aryl (e.g., benzyl), aryl (e.g. phenyl) or C$_{0-4}$ alkyl-C$_{2-9}$ heterocycle. Substitutions are independently chosen. The organic moieties exclude obviously unstable moieties, e.g., —O—O—, except where such unstable moieties are transient species that one can use to make a compound with sufficient chemical stability for one or more of the uses described herein. The substitutions listed above are typically substituents that one can use to replace one or more carbon atoms, e.g., —O— or —C(O)—, or one or more hydrogen atom, e.g., halogen, —NH$_2$ or —OH.

"Thioester" means a moiety that comprises a —C(O)—S— structure. Typically, thioesters as used here comprise an organic moiety containing about 1-50 carbon atoms (e.g., about 2-20 carbon atoms) and 0 to about 10 heteroatoms (e.g., O, S, N, P, Si), where the organic moiety is bonded to a Formula I steroid nucleus at R$^2$ through the —C(O)—S— structure, e.g., organic moiety —C(O)—S— steroid. The organic moiety is as described above for esters.

"Phosphoester" or "phosphate ester" means a moiety that comprises a —O—P(OR$^{PR}$)(O)—O-structure where R$^{PR}$ is hydrogen (—H), a protecting group or an organic moiety as described for esters. Typically, phosphoesters as used here comprise a hydrogen atom, a protecting group, or an organic moiety containing about 1-50 carbon atoms and 0 to about 10 heteroatoms (e.g., O, S, N, P, Si) linked to a Formula I steroid nucleus at R$^1$ through the —O—P(O)(O)—O— structure, e.g., organic moiety-O—P(O)(OH)—O-steroid. The organic moiety is as described above for esters.

"Phosphothioester" means a moiety that comprises a —O—P(SR$^{PR}$)(O)—O— structure where R$^{PR}$ is —H, a protecting group or an organic moiety as described for esters. Typically, phosphothioesters as used here comprise a hydrogen atom, a protecting group or an organic moiety containing about 1-50 carbon atoms and 0 to about 10 heteroatoms (e.g., O, S, N, P, Si) linked to a Formula I steroid nucleus at R$^1$ through the —O—P(O)(O)—O— structure, e.g., organic moiety-O—P(O)(SH)—O-steroid. The organic moiety is as described above for esters.

"Phosphonoester" means a moiety that comprises a —P(OR$^{PR}$)(O)—O— structure where R$^{PR}$ is —H, a protecting group or an organic moiety as described for esters. Typically, phosphonoesters as used here comprise a hydrogen atom, a protecting group or an organic moiety containing about 1-50 carbon atoms and 0 to about 10 heteroatoms (e.g., O, S, N, P, Si) linked to a Formula I steroid nucleus at R$^1$ through the —P(OR$^{PR}$)(O)—O— structure, i.e., organic moiety-P(OR$^{PR}$)(O)—O-steroid. The organic moiety is as described above for esters.

"Phosphiniester" means a moiety that comprises a —P(OR$^{PR}$)—O— structure where R$^{PR}$ is —H, a protecting group or an organic moiety as described for esters. Typically, phosphiniesters as used here comprise a hydrogen atom, a protecting group or an organic moiety containing about 1-50 carbon atoms and 0 to about 10 heteroatoms (e.g., O, S, N, P, Si) linked to a Formula I steroid nucleus at R$^1$-R$^6$ through the —P(OR$^{PR}$)—O— structure, i.e., organic moiety-P(OR$^{PR}$)—O-steroid. The organic moiety is as described above for esters.

"Sulfate ester" means a moiety that comprises a —O—S(O)(O)—O— structure. Typically, sulfate esters as used here comprise a hydrogen atom, a protecting group or an organic moiety containing about 1-50 carbon atoms and 0 to about 10 heteroatoms (e.g., O, S, N, P, Si) linked to a Formula I steroid nucleus at R$^1$ through the —O—S(O)(O)—O— structure, e.g., organic moiety-O—S(O)(O)—O-steroid. The organic moiety is as described above for esters.

"Sulfite ester" means a moiety that comprises a —O—S(O)—O— structure. Typically, sulfite esters as used here comprise an organic moiety containing about 1-50 carbon atoms and 0 to about 10 heteroatoms (e.g., O, S, N, P, Si) linked to a Formula I steroid nucleus at R$^1$ through the —O—S(O)—O— structure, e.g., organic moiety-O—S(O)—O-steroid. The organic moiety is as described above for esters.

"Acyl group" means an organic moiety as described for ester that comprises 1, 2, 3, 4, or more —C(O)— groups. In some embodiments, the —C(O)— group is linked to the steroid nucleus at R, e.g., organic moiety-C(O)—O-steroid.

"Thioacyl" means an organic moiety as described for ester that comprises 1, 2, 3, 4, or more —C(S)— groups. In some embodiments, the —C(S)— group is linked to the steroid nucleus at R, e.g., organic moiety-C(S)—O-steroid.

"Carbonate" means an organic moiety as described for ester that comprises 1, 2, 3, 4, or more —O—C(O)—O— structures. Typically, carbonate groups as used here comprise an organic moiety containing about 1-50 carbon atoms and 0 to about 10 heteroatoms (e.g., O, S, N, P, Si) linked to a Formula I steroid nucleus at R through the —O—C(O)—O— structure, e.g., organic moiety-O—C(O)—O-steroid.

"Carbamate" means an organic moiety as described for ester that comprises 1, 2, 3, 4, or more —NR$^{PR}$—C(O)—O— structures where R$^{PR}$ is —H, a protecting group or an organic moiety. Typically, carbamate groups as used here comprise an organic moiety containing about 1-50 carbon atoms and 0 to about 10 heteroatoms (e.g., O, S, N, P, Si) linked to a Formula I steroid nucleus at R through the —NR$^{PR}$—C(O)—O— structure, e.g., organic moiety-NR$^{PR}$—C(O)—O-steroid.

"Thiocarbonate" means a moiety that comprises an R$^{PR}$S—C(O)—O structure. Typically, thiocarbonate groups as used here comprise an organic moiety containing about 1-50 carbon atoms and 0 to about 10 heteroatoms (e.g., O, S, N, P, Si) linked to a Formula I steroid nucleus at R through the S—C(O)—O structure, e.g., organic moiety-S—C(O)—O-steroid. The organic moiety is as described above for esters.

As used herein, "monosaccharide" means a polyhydroxy aldehyde or ketone having the empirical formula (CH$_2$O)$_n$ where n is 3, 4, 5, 6, or 7. Monosaccharide includes open chain and closed chain forms, but will usually be closed chain forms. Monosaccharide includes hexofuranose and pentofuranose sugars such as 2'-deoxyribose, ribose, arabinose, xylose, their 2'-deoxy and 3'-deoxy derivatives and their 2',3'-dideoxy derivatives. Monosaccharide also includes the 2',3' dideoxydidehydro derivative of ribose. Monosaccharides include the D-, L- and DL-isomers of glucose, fructose, mannose, idose, galactose, allose, gulose, altrose, talose, fucose, erythrose, threose, lyxose, erythrulose, ribulose, xylulose, ribose, arabinose, xylose, psicose, sorbose, tagatose, glyceraldehyde, dihydroxyacetone, and their monodeoxy derivatives such as rhamnose. Monosaccharides are optionally protected or partially protected.

Optionally substituted alkyl group, optionally substituted alkenyl group, optionally substituted alkynyl group, optionally substituted aryl moiety and optionally substituted heterocycle mean substitutions that include $C_{1-20}$ alkyl moieties, $C_{2-20}$ alkenyl moieties, $C_{2-20}$ alkynyl moieties, aryl moieties, $C_{2-9}$ heterocycles or substituted derivatives of any of these. Typical substitutions for these organic groups include 1, 2, 3, 4 or more, usually 1 or 2, —O—, —S—, —NR$^{PR}$—, —C(O)—, —N(R$^{PR}$)$_2$, —C(O)OR$^{PR}$, —OC(O)R$^{PR}$, —OR$^{PR}$, —SR$^{PR}$, —NO$_2$, —CN, —NHC(O)—, —C(O)NH—, —OC(O)—, —C(O)O—, —O-A8, —S-A8, —C(O)-A8, —OC(O)-A8, —C(O)O-A8, =N—, —N=, —OPO$_2$R$^{PR}$, —OSO$_3$H or halogen moieties or atoms, where R$^{PR}$ independently is —H, a protecting group or both R$^{PR}$ together are a protecting group and A8 is $C_{1-8}$ alkyl, $C_{1-8}$ alkenyl, $C_{1-8}$ alkynyl, $C_{1-4}$alkyl-aryl (e.g., benzyl), aryl (e.g. phenyl) or $C_{1-4}$ alkyl-$C_{1-5}$ heterocycle. Substitutions are independently chosen. The organic moieties as described here, and for other any other moieties described herein, exclude obviously unstable moieties, e.g., —O—O—, except where such unstable moieties are transient species that one can use to make a compound with sufficient chemical stability for the one or more of the uses described herein.

Optionally substituted "monosaccharide" comprise any $C_3$-$C_7$ sugar, D-, L- or DL-configurations, e.g., erythrose, glycerol, ribose, deoxyribose, arabinose, glucose, mannose, galactose, fucose, mannose, glucosamine, N-acetylneuraminic acid, N-acetylglucosamine, N-acetylgalactosamine that is optionally substituted at one or more hydroxyl groups. Suitable substitutions include hydrogen, protected hydroxyl, carboxyl, azido, cyano, —O—$C_{1-6}$ alkyl, —S—$C_{1-6}$ alkyl, —O—$C_{2-6}$ alkenyl, —S—$C_{2-6}$alkenyl, optionally protected amine, optionally protected carboxyl, halogen, thiol or protected thiol. The linkage between the monosaccharide the steroid is alpha or beta.

Optionally substituted "oligosaccharide" comprises two, three, four, or more of any C3-C7 sugars that are covalently linked to each other. The linked sugars may have D-, L- or DL-configurations. Suitable sugars and substitutions are as described for monosaccharides. The linkage between the oligosaccharide and the steroid is alpha or beta, as are the linkages between the monosaccharides that comprise the oligosaccharide.

Nucleoside includes 3TC, AZT, D4T, ddI, ddC, G, A, U, C, T, dG, dA, dT, and dC.

Polymer includes biocompatible organic polymers, e.g., PEGs and polyhydroxyalkyl polymers.

PEG means an ethylene glycol polymer that contains about 20 to about 2000000 linked monomers, typically about 50-1000 linked monomers, usually about 100-300. Polyethylene glycols include PEGs containing various numbers of linked monomers, e.g., PEG20, PEG30, PEG40, PEG60, PEG80, PEG100, PEG115, PEG 200, PEG 300, PEG400, PEG500, PEG600, PEG 1000, PEG1500, PEG2000, PEG 3350, PEG4000, PEG4600, PEG5000, PEG6000, PEG8000, PEG11000, PEG12000, PEG2000000, and any mixtures thereof.

Salt(s) as used in the present invention, including the embodiments, include salts and complexes of the compounds of Formula I, including pharmaceutically acceptable or salts that are relatively non-toxic. Some of the invention compounds have one or more moieties that carry at least a partial positive or negative charge in aqueous solutions, typically at a pH of about 4-10, that can participate in forming a salt, a complex, a composition with partial salt and partial complex properties or other noncovalent interactions, all of which we refer to as a "salt(s)." Salts are usually biologically compatible or pharmaceutically acceptable or non-toxic, particularly for mammalian cells. Salts that are biologically toxic are optionally used with synthetic intermediates of invention compounds. When a water-soluble composition is desired, monovalent salts are usually used.

Metal salts typically are prepared by reacting the metal hydroxide with a compound of the present invention. Examples of metal salts that are optionally prepared in this way are salts containing Li$^+$, Na$^+$, and K$^+$. A less soluble metal salt can be precipitated from the solution of a more soluble salt by adding a suitable metal compound. The salts of the present invention may be formed from acid addition of certain organic acids, such as organic carboxylic acids, and inorganic acids, such as alkylsulfonic acids or hydrogen halide acids, to acidic or basic centers on the invention compounds, such as basic centers on the pyrimidine base analogs of the invention compounds. Metal salts include ones containing Na$^+$, Li$^+$, K$^+$, Ca$^{++}$ or Mg$^{++}$. Other metal salts may contain aluminum, barium, strontium, cadmium, bismuth, arsenic, or zinc ion.

Salt(s) of the invention compounds may comprise a combination of appropriate cations such as alkali and alkaline earth metal ions or ammonium and quaternary ammonium ions with the acid anion moiety of the phosphoric acid or phosphonic acid group, which may be present in the polymers or monomers of the present invention.

Salts are produced by standard methods, including dissolving free base in an aqueous, aqueous-alcohol or aqueous-organic solution containing the selected acid, optionally followed by evaporating the solution. The free base is reacted in an organic solution containing the acid, in which case the salt usually separates directly or one can concentrate the solution.

Suitable amine salts include amines having sufficient basicity to form a stable salt, usually amines of low toxicity including trialkyl amines (tripropylamine, triethylamine, trimethylamine), procaine, dibenzylamine, N-benzyl-beta-phenethylamine, ephenamine, N,N'-dibenzylethylenediamine, N-ethylpiperidine, benzylamine, and dicyclohexylamine.

Salts include organic sulfonic acid or organic carboxylic acid salts, made for example by addition of the acids to basic centers, typically amines. Exemplary sulfonic acids include $C_{6-16}$ aryl sulfonic acids, $C_{6-16}$ heteroaryl sulfonic acids and $C_{1-16}$ alkyl sulfonic acids such as phenyl sulfonic acid, a-naphthalene sulfonic acid, beta-naphthalene sulfonic acid, (S)-camphorsulfonic acid, methyl ($CH_3SO_3H$), ethyl ($C_2H_5SO_3H$), n-propyl, i-propyl, n-butyl, s-butyl, i-butyl, t-butyl, pentyl, and hexyl sulfonic acids. Exemplary organic carboxylic acids include $C_{1-16}$ alkyl, $C_{6-16}$ aryl carboxylic acids and $C_{4-16}$ heteroaryl carboxylic acids such as acetic, glycolic, lactic, pyruvic, malonic, glutaric, tartaric, citric, fumaric, succinic, malic, maleic, oxalic, hydroxymaleic, benzoic, hydroxybenzoic, phenylacetic, cinnamic, salicylic, nicotinic, and 2-phenoxybenzoic.

The salts of the present invention include those made from inorganic acids, e.g., HF, HCl, HBr, HI, $H_2SO_4$, $H_3PO_4$, $Na_2CO_3$, $K_2CO_3$, $CaCO_3$, $MgCO_3$, and $NaClO_3$. Suitable anions, which are optionally present with a cation such a Ca$^{++,}$ Mg$^{++,}$ Li$^+$, Na$^+$, or K$^+$, include arsenate, arsenite formate, sorbate, chlorate, perchlorate, periodate, dichromate, glycodeoxycholate, cholate, deoxycholate, desoxycholate, taurocholate, taurodeoxycholate, taurolithocholate, tetraborate, nitrate, nitrite, sulfite, sulfamate, hyposulfite, bisulfite, metabisulfite, thiosulfate, thiocyanate, silicate, metasilicate, CN$^-$, gluconate, gulcuronate, hippurate, picrate, hydrosulfite, hexafluorophosphate, hypochlorite, hypochlorate, borate, metaborate, tungstate, and urate.

Salts also include salts of the invention compound with one or more amino acids. Many amino acids are suitable, especially the naturally-occurring amino acids found as protein components, although the amino acid typically is one bearing a side chain with a basic or acidic group, e.g., lysine, arginine, histidine, or glutamic acid, or a neutral group such as glycine, serine, threonine, alanine, isoleucine, or leucine.

The invention compositions include compounds in their un-ionized, as well as zwitterionic form, and combinations with stoichimetric amounts of water as in hydrates.

Stereoisomers of the compounds of the present invention (Formula I compounds) include enriched or resolved optical isomers at any or all asymmetric atoms as are apparent from the depictions. Both racemic and diasteromeric mixtures, as well as the individual optical isomers can be isolated or synthesized so as to be substantially free of their enantiomeric or diastereomeric partners, and these are all within the scope of the present invention. Chiral centers may be found in invention compounds at, for example, R and X.

As used herein, "innate immunity" refers to one or more components typically associated with nonspecific immune defense mechanisms in a subject. These components include the alternate complement pathway, e.g., Factor B, Factor D and properdin; NK cells, phagocytes (monocytes, macrophages), neutrophils, eosinophils, dendritic cells, fibrocytes; anti-microbial chemicals, e.g., defensins; physical barriers-skin, mucosal epithelium; and certain interleukins, chemokines, and cytokines. Innate immunity plays a role in resistance to intracellular parasite infections, e.g., white blood cell infection, a liver infection, and other infections, e.g., lymph node infections. Enhancement of innate immunity mechanism by Formula I compounds or method described herein may enhance phagolysosome fusion or movement, which some pathogens, e.g., intracellular bacteria such as mycobacteria, or *Listeria* inhibit.

As used herein, references to CD molecules, specific immune cell subsets, immune responses, and the like, generally use nomenclature that applies to molecules, cells, or the like that are found in humans. Analogs or counterparts of such molecules, cells, or the like in other species may have a differing nomenclature, but are included in the present invention. A description of the nomenclature and function of various CD molecules and immune cell subsets are as found in the scientific literature. References to Th0, Th1 or Th2 cells and references to Th1 or Th2 immune responses in the context of human patients refers to the human counterparts of the murine Th0, Th1 or Th2 immune cells or responses. For reviews see, e.g., Carli, M. et al, "HUMAN TH1 AND TH2 CELLS: FUNCTIONAL PROPERTIES, REGULATION OF DEVELOPMENT AND ROLE IN AUTOIMMUNITY," Autoimmunity, 18 (4), 301-308 (1994)

"Immunosuppressive molecule" means molecules such as cyclosporin, cyclohexamide, mitomycin C, adriamycin, taxol, and amphotericin B. These molecules tend to have toxicities toward the immune system and are directly or indirectly immunosuppressive, i.e., toxic to dividing cells or they can downregulate immunity.

"Steroid receptor" means a gene product, typically a protein monomer or dimer that can bind to a ligand, e.g., a natural steroid or an analog thereof, such as Formula I compounds. Steroid receptors include orphan steroid receptors. Orphan steroid receptors are proteins for which the natural ligand or biological function is at least partially unknown. As used here, steroid receptors include homodimers, e.g., SXR and (CARbeta)$_2$, and heterodimers, e.g., PXR-CARbeta or RXR-CARbeta. Steroid receptors also include isoforms, e.g., PXR. 1 and PXR.2 for the PXR receptor, and homologs of the steroid receptors, e.g., the homolog of CARbeta known as MB67. Isoforms are typically generated by different splicing pathways for a nuclear RNA from one gene, while homologs are typically a distinct copy of a steroid receptor gene, where the gene copy encodes only relatively small differences compared to the reference steroid receptor gene product. Such differences are most often found in areas other than the dimerization region and the steroid binding region of the steroid receptor's structure. Typically, isoforms and homologs bind the same or similar ligands as the reference gene product or steroid receptor. Steroid receptors may be of human or animal origin, e.g., obtained from cells, tissues or cDNA expression libraries derived from cells or tissues of any primate, rodent (including murine), avian, ovine, bovine, equine, canine, or feline species or any of the species or any species within any group (e.g., Family or Genus) of species mentioned elsewhere herein or in any reference cited herein.

In one embodiment of the present invention, BEA is milled to an average particle size of about 0.01-200 μm, or about 0.1-10 μm or about 0.5-5 μm. Average particle size or diameter for milled BEA may thus be relatively small, e.g., about 0.03-2.0 μm or about 0.1-1.0 μm, or somewhat larger, e.g., about 0.5-5.0 μm or about 1-5.0 μm. Milled BEA is suitable for preparing solid formulations and parenteral and aerosol formulations for human or veterinary use. The milled material facilitates suspension of BEA in water and excipients and facilitates mixing with solids or solid excipients.

While it is possible to administer BEA as a pure compound to a subject, it is usually presented as a solid formulation. Formulations is typically used to prepare unit dosages, e.g., tablets, capsules, or lozenges for oral, buccal, or sublingual administration, that comprise about 10-1000 mg or typically about 25-400 mg of BEA. Alternatively, embodiments include a liquid product for parenteral (e.g., subcutaneous, subdermal, intramuscular, intraperitoneal) and aerosol administration. Such products for parenteral and aerosol administration typically comprise BEA at a concentration of about 10-170 mg/mL, usually at about 20-110 mg/mL or about 30-100 mg/mL, and optionally one or more of a salt, buffer or bacteriostat or preservative (e.g., NaCl, BHA, BHT or EDTA).

In general, the Formula I compounds that are present in the compositions and formulations of the present invention are suspensions in water with excipients. However, in some embodiments, e.g., transient composition, the Formula I compound is suspended in water with excipients and then lyophilized to yield a water dispersible dry composition.

The compositions and formulations of the present invention suitable for parenteral delivery of Formula I compounds to humans or animals typically comprise two, three, or more excipients. Exemplary embodiments include (1) any two, three, or four of propylene glycol, PEG200, PEG300, ethanol and benzyl benzoate; and (2) any two, three, or four of propylene glycol, PEG100, PEG200, PEG300, PEG400, and benzyl benzoate.

R includes moieties, e.g., esters, thioesters, carbonates, amino acids, peptides, and/or carbamates, that are chemically and/or enzymatically hydrolyzable, often under physiological conditions. Such moieties are independently chosen. Typically, these moieties will give rise to —OH, at the R positions of the steroid nucleus. Embodiments of Formula I compounds include ones where R is a hydrolyzable moiety (e.g., ester, thioester, carbonate, amino acid, peptide or carbamate).

Regarding metabolites, also falling within the scope of the present invention are the in vivo metabolites of the compounds described herein, to the extent such products are novel and unobvious over the prior art. Such products may result for example from the oxidation, reduction, hydrolysis, amidation, esterification, and the like of the administered Formula I compound, due to enzymatic or chemical processes. Accordingly, the present invention includes novel and unobvious compounds produced by a process comprising contacting a compound of the present invention with a subject, e.g., a human, rodent, or a primate, for a period of time sufficient to yield a metabolic product thereof. Such products typically are identified by preparing a radiolabeled (e.g. $^{14}C$, $^{3}H$, $^{131}I$, $^{32}P$, $^{35}S$ or $^{99}Tc$) compound of the present invention, administering it parenterally in a detectable dose (e.g. greater than about 0.5 mg/kg) to an animal such as rat, mouse, guinea pig, primate, or to a human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS, HPLC or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the present invention even if they possess no therapeutic activity of their own.

Formulations and compositions for preparing formulations are provided in the present invention. While it is possible for the active ingredient(s) to be administered alone, it is usual to present them as pharmaceutical formulations. The invention formulations, both for veterinary and for human use, comprise at least one active ingredient, i.e., a Formula I compound, together with one or more acceptable excipients therefor and optionally other therapeutic ingredients.

Another aspect of the present invention relates to compositions comprising one or more pharmaceutically acceptable excipients or carriers. One or more Formula I compound(s) (also referred to as the "active ingredient(s)") are administered by any route appropriate to the condition to be treated. Suitable routes for the aqueous suspension formulations and other Formula I compound formulations include oral, rectal, nasal, topical (including buccal and sublingual), vaginal, parenteral (including subcutaneous, intramuscular, intradermal, intrathecal and epidural), and aerosol. In general, the aqueous suspension formulations are delivered by a parenteral route. In other embodiments, such as the present invention intermittent dosing methods, the Formula I compound(s) may be present as a aqueous suspension formulation, a dry solid formulation that is an oral, topical, or parenteral formulation. It is appreciated that the preferred route may vary with, for example, the subject's pathological condition or weight or the subject's response to therapy with a Formula I compound or other therapy appropriate to the circumstances.

The formulations include those suitable for the foregoing administration routes. The formulations may conveniently be presented in unit dosage form and may be prepared by any of the methods well known in the art of pharmacy. Techniques, excipients and formulations generally are found in, e.g., Remington's Pharmaceutical Sciences, Mack Publishing Co., Easton, Pa. 1985, $17^{th}$ edition, Nema et al., PDA J. Pharm. Sci. Tech. 1997 51:166-171. Methods to make invention formulations include the step of bringing into association an active ingredient(s) with the excipient(s). In general, the formulations are prepared by uniformly and intimately bringing into association the active ingredient with liquid excipients or finely divided solid excipients or both, and then, if appropriate, shaping the product.

Invention formulations suitable for oral administration are prepared as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient(s) may also be presented as a bolus, electuary, or paste.

A tablet is made by compression or molding, optionally with one or more accessory ingredients. Compressed tablets may be prepared by compressing in a suitable machine the active ingredient(s) in a free-flowing form such as a powder or granules, optionally mixed with a binder, lubricant, inert diluent, preservative, surface active, or dispersing agent. Molded tablets may be made by molding in a suitable machine a mixture of the powdered active ingredient(s) moistened with an inert liquid diluent. The tablets may optionally be coated or scored and optionally are formulated so as to provide slow or controlled release of the active ingredient(s) therefrom.

Formulations suitable for topical administration to the eye also include eye drops wherein the active ingredient(s) is suspended in a suitable excipient(s), especially an aqueous solvent for active ingredient(s) that comprise one or more charges at pH values near neutrality, e.g., about pH 6-8. The active ingredient(s) is typically present in such formulations in a concentration of about 0.5-20% w/w, typically about 1-10% w/w, often about 2-5% w/w.

Formulations suitable for topical administration in the mouth include lozenges comprising the active ingredient in a flavored basis, usually sucrose and acacia or tragacanth; pastilles comprising the active ingredient(s) in an inert basis such as gelatin and glycerin, or sucrose and acacia; and mouthwashes comprising the active ingredient in a suitable liquid excipient(s).

Formulations for rectal administration may be presented as a suppository with a suitable base comprising for example cocoa butter or a salicylate.

Formulations suitable for intrapulmonary or nasal administration have a particle size for example in the range of 0.01 to 500 microns (including average particle sizes in a range between 0.01 and 500 microns in 0.1 micron or other increments, e.g., 0.05, 0.1, 0.5, 1, 1.5, 2.0, 2.5, 3.0, 3.5, 4.0, 4.5, 5.0, 6, 7, 8, 9, 10, 20, 25, 30, 35, 50, 75, 100, etc. microns), which is administered by rapid inhalation through the nasal passage or by inhalation through the mouth so as to reach the alveolar sacs. Suitable micronized formulations include aqueous or oily solutions or suspensions of the active ingredient(s). Formulations suitable for aerosol, dry powder or tablet administration may be prepared according to conventional methods and may be delivered with other therapeutic agents such as compounds heretofore used in the treatment or prophylaxis of viral or other infections as described herein. Such formulation may be administered, e.g., orally, parenterally (i.v., i.m., s.c.), topically, aerosolly, or by a buccal route.

Formulations suitable for vaginal administration may be presented as pessaries, tampons, creams, gels, pastes, foams, or spray formulations containing in addition to the active ingredient(s) such excipients as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example, sealed ampules and vials, and may be stored in a freeze-dried (lyophilized) condition requiring only the addition of the sterile liquid excipient, for example water for injection, immediately prior to use. Extemporaneous injection solutions and suspensions are prepared from sterile powders, granules and tablets of the kind previously described. Unit dosage formulations are those containing a daily dose or unit daily sub-dose, as recited herein, or an appropriate fraction thereof, of the active ingredient(s).

It should be understood that, in addition to the ingredients particularly mentioned above, the invention formulations may include other agents or excipients conventional in the art having regard to the type of formulation in question, for example those suitable for oral administration may include flavoring agents.

The present invention further provides veterinary compositions comprising at least one active ingredient as above defined together with a veterinary excipient(s) therefor. Veterinary excipients are materials useful for the purpose of administering the composition and may be solid, liquid or gaseous materials that are otherwise inert or acceptable in the veterinary art and are compatible with the active ingredient(s). These veterinary compositions may be administered orally, parenterally or by any other desired route.

The formulations of the present invention include controlled release pharmaceutical formulations containing an active ingredient(s) ("controlled release formulations") in which the release of the active ingredient(s) is controlled and regulated to allow less frequency dosing or to improve the pharmacokinetic or toxicity profile of a given active ingredient(s).

An effective dose of active ingredient(s) depends at least on the nature of the condition being treated, toxicity, whether the compound(s) is being used prophylactically (lower doses) or against an active infection or condition, the method of delivery, and the pharmaceutical formulation, and will be determined by the clinician using conventional dose escalation studies. It can be expected to be from about 0.05 to about 30 mg/kg body weight per day. For example, for topical delivery the daily candidate dose for an adult human of approximately 70 kg body weight will range from about 1 mg to about 500 mg, generally between about 5 mg and about 40 mg, and may take the form of single or multiple doses or administration sites.

Embodiments include formulations that comprise a liposome or lipid complex that comprises a Formula I compound (s), e.g., BEA or an ester, carbamate, carbonate, amino acid or peptide thereof. Such formulations are prepared according to known methods, e.g., U.S. Pat. Nos. 4,427,649, 5,043,165, 5,714,163, 5,744,158, 5,783,211, 5,795,589, 5,795,987, 5,798,348, 5,811,118, 5,820,848, 5,834,016, and 5,882,678. The liposomes optionally contain an additional therapeutic agent(s), e.g., amphotericin B, cis-platin, adriamycin, a protease inhibitor, a nucleoside or a nucleotide analog, such as one of those mentioned herein. Formulations that comprise liposomes can be delivered to a subject by any standard route, e.g., oral, aerosol or parenteral (e.g., s.c., i.v. or i.m.).

Therapeutic applications. The Formula I compounds, or the biologically active substances produced from these compounds by hydrolysis or metabolism in vivo, have a number of clinical and non-clinical applications. The compounds are generally useful to enhance Th1 immune responses or to reduce Th2 immune responses. As used herein, reference to Th1 or Th2 immune responses means such responses as observed in mammals generally and not as observed in the murine system, from which the Th1 and Th2 terminology originated. Thus, in humans, Th1 cells preferentially display chemokine receptors CXCR3 and CCR5, while Th2 cells preferentially express the CCR4 molecule and a smaller amount of the CCR3 molecule.

Other uses for the Formula I compound(s) include administering the compound(s) to a subject who suffers from a pathological condition(s). The treatment may treat or ameliorate the source of the condition(s) and/or symptoms associated with the pathological condition(s) such as infection with a pathogen(s) (viruses, bacteria, fungi), a malignancy, unwanted immune response, i.e., an immune response that causes pathology and/or symptoms, e.g., autoimmune conditions or allergy or conditions such as hypoproliferation conditions, e.g., normal or impaired tissue growth, or wound healing or burn healing, or in immunosuppression conditions, e.g., conditions characterized by an absence of a desired response and/or an inadequate degree of a desired response.

Many cancers or malignancies are associated with an unwanted Th2 immune response or a deficient Th1 response. An insufficient Th1 immune response may play a role in the capacity of malignant cells to escape immune surveillance. These conditions include non-small cell lung cancer, bronchogenic carcinoma, renal cell cancer or carcinoma, lymphoma, glioma, melanoma, pancreatic or gastric adenocarcinoma, human papillomavirus associated cervical intraepithelial neoplasia, cervical carcinoma, hepatoma and cutaneous T-cell lymphoma (mycosis fungoides, Sezary syndrome).

In some of these embodiments, the subject's hyperproliferation or malignant condition may be associated with one or more pathogens. For example, hepatocellular carcinoma associated with HCV or HBV, Kaposi's sarcoma associated with HIV-1 or HIV-2, T cell leukemia associated with HTLV I, Burkitt's lymphoma associated with Epstein-Barr virus or papillomas or carcinoma associated with papilloma viruses (HPV 6, HPV 11, HPV 16, HPV 18, HPV 31, HPV 45) or gastric adenocarcinoma or gastric MALT lymphoma associated with *Helicobacter pylori* infection. In other embodiments, the Formula I compound(s) is administered to a subject who has a hyperproliferation condition that appears to not be associated with a pathogen, e.g., melanoma, or a cancer or precancer arising in the throat, esophagus, stomach, intestine, colon, ovary, lung, breast, or central nervous system.

In an exemplary embodiment, human patients suffering from melanoma or melanoma precursor lesions are treated with a topical cream formulation containing 2-20% BEA (w/w). The cream is applied to primary nevi (dysplastic nevi or common acquired nevi), primary cutaneous melanomas, secondary cutaneous melanomas, and the skin surrounding the nevi or melanomas. The areas to be treated are washed with soap or swabbed with an alcohol (e.g., ethanol or isopropanol) prior to administering the cream, when this is practical. About 0.1-0.4 g of cream, depending on the size of the treated area, is applied once or twice per day per treated region or lesion for about 10-20 days. The cream is left undisturbed at the administration site for about 15-30 minutes before the patient resumes normal activity. Progression of the nevi and melanomas is retarded in the majority of patients and significant regression is observed for some lesions. Following initial treatment, the formulation is administered every other day for at least 1 to 4 months using the same dosing described for the initial round of treatment. For these patients, standard therapy to treat precursor lesion or melanoma, e.g., dimethyl triazeno imidazole carboxamide or nitrosoureas (e.g., BCNU, CCNU), is optionally started or continued according to the recommendations of the patient's doctor and with the patient's informed approval. In cases where a tumor or precursor lesion is surgically removed and the site has sufficiently healed, the patient optionally continues using the topical formulation at the site and the adjacent surrounding area every other day for at least 1 to 4 months. In some of these embodiments, a Formula I compound(s) is administered daily continuously as an oral composition or formulation, e.g., for a Formula I compound(s) that is a new compound per se. BEA is optionally also administered systemically using, e.g., a formulation described in the examples below to deliver 1-5 mg/kg/day every other day for about 1 week to about to 4 months, e.g., in the case of malignant melanoma. In another embodiment, a mouse model of multiple myeloma based on M-Spike, or M-protein, has been shown in clinical trials to a predictor of effectiveness of an anti-multiple myeloma drug. (Chesi, M. et al., (2012). BEA has shown a 40% reduction on M-Spike in this in-vivo model (Example 11), indicating BEA is effective in treating multiple myeloma.

In some embodiments, Formula I compound(s) formulation is proven in in-vivo model that it's effective in treating TB and MAP related disease by modulating the innate immunity. BEA exerts beneficial effects on a spectrum of diseases involving seemingly different disease processes due to its action on fundamental biological signaling pathways involving autophagy and inter-connected intracellular signaling pathways. BEA's ability to stimulate innate immunity while re-establishing control of dysregulated, unproductive inflammation is key to its efficacy. Many acute and chronic infectious, neoplastic, and idiopathic chronic inflammatory diseases are associated with dysregulated immune signaling associated with compromised autophagy and dysregulated signaling pathways, both intracellular and extracellular.

In one embodiment, acting as a hormone, BEA elicits responses in different cell types throughout the host resulting in restoration of 'dynamic homeostasis' of the immune network. This term implies that BEA restores the ability of the immune system to function correctly as evidenced by BEA's ability to enhance innate immunity, down-regulate unproductive inflammation, promote Th1 cell mediated immune processes and more effectively respond to threats from microbial PAMPS (pathogen associated molecular patterns) and neoplastic DAMPS (danger associated molecular patterns) interpreted through PRR (pattern recognition receptors) pathways.

In another embodiment, BEA's influence on dendritic cells and macrophages as professional antigen presenting cells influencing downstream signaling of the adaptive immune system is central to its global systemic effect on restoring immune dynamic homeostasis. *Mycobacterium avium* ss. paratuberculosis (MAP) is an acid-fast staining small rod-shaped bacterium. It has been associated with Crohn's disease, rheumatoid arthritis, Blau syndrome, type 1 diabetes, Hashimoto thyroiditis, multiple sclerosis and Sarcoidosis. It also causes Johne's disease in cattle and other ruminants.

In yet another embodiment, BEA can be used to inhibit bacterial proliferation and increase expression of TNF-alpha, IFN-gamma, and iNOS of mice infected with MTB. See Hernandez-Pando, et al. (2005).

In another embodiment, BEA can be used to treat not only MTB, but also Crohn's disease, rheumatoid arthritis, Blau syndrome, type 1 diabetes, Hashimoto thyroiditis, multiple sclerosis and Sarcoidosis, as well as Johne's disease, as confirmed in the animal model for Inflammatory Bowel Diseases (IBD) described in Example 5 of the present invention.

Insufficient Th1 immune responses are often associated with viral infection. Viral infections may arise from DNA or RNA viruses, e.g., herpesviruses, hepadnaviruses, adenoviruses, retroviruses, togaviruses, aiphaviruses, arboviruses, flaviviruses, rhinoviruses, papillomaviruses and/or pestiviruses. As used herein, retroviruses include human and animal viruses, e.g., HIV-1, HIV-2, LAV, human T-cell leukemia virus I ("HTLV I"), HTLV II, HTLV III, SIV, SHIV, FIV, FeLV. Additional viruses, including their genogroups, clades, isolates, strains and so forth, that may establish a virus infection include human hepatitis C virus ("HCV"), human hepatitis B virus ("HBV"), human hepatitis A virus ("HAV"), duck hepatitis virus, woodchuck hepatitis virus, human ("HPV", e.g., HPV 6, HPV 11, HPV 16, HPV 18, HPV 31, HPV 45) or animal papilloma viruses, Poliovirus, Herpes simplex virus 1 ("HSV-1"), Herpes simplex virus 2 ("HSV-2"), human Herpesvirus 6 ("HHV-6"), human Herpesvirus 8 ("HHV-8"), Dengue virus (types 1-4), Western Equine Encephalitis Virus, Japanese Encephalitis Virus, Yellow Fever Virus and Bovine Viral Diarrhea Virus.

Other conditions where an immune imbalance or an excessive Th2 immune response is involved include autoimmune diseases such as SLE (systemic lupus erythematosus), osteoporosis, multiple sclerosis, myasthenia gravis, Graves disease, mite-associated ulcerative dermatitis, rheumatoid arthritis and osteoarthritis. Excessive Th2 immune responses are also associated with an unwanted symptom or pathology, e.g., fatigue, pain, fever or an increased incidence of infection, that is associated with aging, allergy and inflammation conditions such as allergic bronchopulmonary aspergillosis in cystic fibrosis patients, atopic asthma, allergic respiratory disease, allergic rhinitis, atopic dermatitis, subepithelial fibrosis in airway hyperresponsiveness, chronic sinusitis, perennial allergic rhinitis, Crohn's disease (regional enteritis), ulcerative colitis, inflammatory bowel disease, fibrosing alveolitis (lung fibrosis).

Other clinical indications that have an association with or have a symptom(s) that is consistent with an excessive Th2 immune response, e.g., fatigue, pain, fever or an increased incidence of infection, are schizophrenia, acute myelitis, sarcoidosis, burns, trauma (e.g., bone fracture, hemorrhage, surgery) and immune responses to xenotransplantation. This common underlying immune component in at least part of the pathology of all of these conditions allows a single agent to be effectively used to treat the condition or to treat one or more symptoms that are associated with insufficient Th1 responses or with excessive Th2 responses. In all of the conditions where an insufficient Th1 response or an unwanted Th2 response is present, amelioration of one or more symptoms associated with the condition is accomplished by administering an effective amount of a Formula I compound according to the methods described herein.

Thus, one may intermittently administer a Formula I compound using a formulation and a route of administration as described herein.

In some applications, the Formula I compound(s) may directly and/or indirectly interfere with replication, development or cell-to-cell transmission of a pathogen such as a virus or a parasite (malaria). Improvement in a subject's clinical condition may arise from a direct effect on an infectious agent or on a malignant cell. Interference with cellular replication can arise from inhibition of one or more enzymes that a parasite or an infected cell uses for normal replication or metabolism, e.g., glucose-6-phosphate dehydrogenase, which affects cellular generation of NADPH (see, e.g., Raineri et al., Biochemistry 1970 9: 2233-2243). The effect may contribute to cytostatic effects that some Formula I compounds can have. Modulation of cellular enzymes expression or activity may also interfere with replication or development of a pathogen, e.g., HIV or malaria parasites or with replication or development of neoplastic cells, e.g., inhibition of angiogenesis. Clinical improvement will also generally result from an enhanced Th1 immune response.

The therapeutic use of BEA arises from its effects on the immune system. BEA stimulates autophagy in macrophages, enhances innate immunity, regulates unproductive inflammation and biases the immune response towards a Th1 response (IFN-gamma, cellular immune pathways). The ability to influence these fundamental aspects of immunity make it useful in disease processes involving infections and dysregulated inflammation. In general, BEA will be useful in treating trauma, infections (viral, bacterial, protozoa, fungal and helminths), neoplasia, metabolic, autoimmune, neuroinflammatory and inflammatory vascular disorders. Specific indications include *Mycobacterium tuberculosis* and non-tuberculosis mycobacteria, chlamydial infections, bacterial pneumonias, Inflammatory Bowel Disease (Crohn's and Ulcerative Colitis), Rheumatoid Arthritis, non-alcoholic fatty liver disease, multiple sclerosis and Alzheimer disease. Essentially, BEA may be helpful in any disease involving inflammation and dysregulated immunity.

Related embodiments include BEA particles and one or more excipients suitable for human pharmaceutical use or for veterinary use. Another related embodiment includes aqueous suspension formulations and water dispersible dry compositions of BEA particles and one or more excipients for parenteral or aerosol administration. The BEA particle sizes range from 0.01 μm to 100 μm, preferably 0.05 μm to 10 μm, more preferably 0.01 μm to 5 μm.

The formulation of the present invention is an aqueous suspension for parenteral and aerosol administration. It uses water as solvent in the course of preparation and in storage. Contrary to literature teaching, this aqueous based suspension formulation and water dispersible dry composition of BEA is stable based on its stability studies (as shown in the following Example 2).

The non-aqueous BEA formulations cause severer pain and injection site irritations because of the organic solvent used. The drug substance (BEA) precipitates out of solution immediately after injection. The resulting BEA solid in tissues also contributes to severe pain and injection site irritation. See Stickney D. R., et al. (2007); Reading C., et al. (2006); Frincke J. M., et al. (2007); Ahlem, C. et al., US2003060425A1.

In the stability test of reported non-aqueous formulation in US2003060425A1 embodiment 1, it is found that it is not stable and easy to degrade when water presents, even with as little as 0.1%. The aqueous suspension formulation and water dispersible dry composition of BEA particles of the present invention use water as solvent in the process of preparation and storage instead of non-aqueous solvent. It has shown remarkable stability in spite of high water content (>90%) as shown in Example 2 of the present invention.

Compared with the reported non-aqueous formulation of US2003060425A1, the aqueous suspension formulation of BEA particles of the present invention does not cause injection site irritation and well absorbed by the body. It significantly reduces patient's pain and improves patient compliance. It also eliminates or reduces the damage to the tissues, which is extremely important for long term uses as shown in Example 4 in the present invention.

In the DSS induced rat colitis model, the aqueous suspension formulation of BEA particles of the present invention showed excellent efficacy with no apparent toxicity. It significantly reduced the number of animals with bloody stools and increased the colon length that is shorten by the diseases. No significant loss of body weight of the group treated with this formulation. It has better efficacy than the standard treatment of Dexamethasone with less toxicity. The blood chemistry analysis shows that the aqueous suspension formulation of BEA particles of the present invention significantly reduced the white blood cell, which indicated the test drug is effective for the treatment of inflammation. It significantly increased the macrophage cell count, which indicates the test drug is effective for immunodeficiency. It significantly reduced the IL-6 level and improved IL-6/TNF-alpha level, indicating the enhanced Th1 and suppressed Th2 response, which means the improvement of immune environment. The immuno organ weight analysis shows that the aqueous suspension formulation of BEA particles of the present invention does not have any effect on atrophy of thymus but significantly inhibited the enlargement of spleen, which indicates the test drug is effective for the treatment of inflammation as shown in Example 5 in the present invention.

The preliminary dog PK studies indicate that the aqueous suspension formulation of BEA particles of the present invention has much higher BEA exposure in blood and longer half-life than the reported non-aqueous formulation, indicating it has better properties and bioavailability as shown in Example 6 in the present invention.

In the in vitro studies, the aqueous suspension formulation of BEA particles of the present invention improved the macrophage's ability to kill bacilli and significantly reduced the number of intracellular live bacilli as shown in Example 7 in the present invention.

In parallel efficacy studies in Mouse *M. Tuberculosis* Model, the aqueous suspension formulation of BEA particles of the present invention is well tolerated and showed equal or better efficacy than the reported non-aqueous formulation in vivo. It should be noted that the aerosol administration (intratracheal) has better effect than parenteral administration (subcutaneous) as shown in Example 8 in the present invention.

Over all, the aqueous suspension formulation and water dispersible dry composition of BEA particles of the present invention has unusual and unexpected stability in aqueous. It can be stored at room temperature. It improves the properties such as PK significantly. It causes no or little injection site irritation. It has also demonstrated better efficacy both in vivo and in vitro compared with reported non-aqueous formulation. The results indicate that it works as an immune modulator. It enhances Th1 response and reduces Th2 response. It stimulates macrophage. It shows the anti-inflammatory property. It improves the innate immunity and reduces immunodeficiency.

In one embodiment of the present invention, an aqueous suspension formulation and a water dispersible dry injectable composition of a compound(s) in Formula I comprises water. In another embodiment of the present invention, an aqueous suspension formulation and a water dispersible dry injectable composition of BEA comprises water. One embodiment of the present invention provides an aqueous suspension formulation and a water dispersible dry injectable composition of BEA particles. The characteristics are that these compositions and formulations contains:

(a) BEA particles: in the present invention, 90% of the BEA particles are smaller than 15 µm; preferably 90% of the particles are smaller than 10 µm, 90% of the particles are smaller than 5 µm is more preferred.

(b) Surfactant: the surfactant of the composition is one or several mixed substances of poloxamers, polysorbate, polyoxyethylated castor oil polyoxyethylene hydrogenated castor oil, polyethylene glycol (PEG)-8-octylic acid/decanoic acid and polyethylene glycol (PEG) hydroxy stearic acid ester, egg yolk lecithin, soybean lecithin, sodium oleate and bile salt. Poloxamer, polysorbate, polyethylene glycol (PEG) hydroxy stearic acid ester are preferred.

(c) Suspending agent: suspending agent is one or several mixed substances of cellulose derivatives such as methylcellulose, hydroxyethylcellulose, carboxymethylcellulose, sodium carboxymethylcellulose, microcrystalline cellulose), polyethylene glycol (PEG), polyvinylpyrrolidone (PVP), gelatin, alginates, acacia, tragacanth, xanthan gum, bentonite, carbomer, carrageenan, or their mixture.

(d) Other pharmaceutical excipients: the composition could contain other pharmaceutical excipients as well, for examples, water for injection, pH regulator, osmotic pressure regulator, freeze-drying protective additive, sequestering agent, antioxidant, preservative, one or more of other medicinal ingredients.

Preferably, the osmotic pressure regulator may be one or more of the glucose, sucrose, trehalose, fructose, mannitol, sorbitol, xylitol, glycerin, and sodium chloride; the freeze-drying protective additive may be one or more of the glucose, sorbitol, mannitol, lactose, sucrose, trehalose, fructose, glycine, and albumin; the pH regulators may be one or more of sodium hydroxide, hydrochloric acid, phosphoric acid, acetic acid, ascorbic acid, citric acid, lactic acid, amino acid and its salts; the sequestering agent may be one or more of ethylenediamine tetraacetic acid and its salts; the antioxidant may be one or more of ethylenediamine tetraacetic acid salt, benzyl alcohol, p-hydroxy benzoic acid esters, cross-linked with tertiary butyl alcohol, phenol, cresol, and benzoic acid salt; and the preservative may be Vitamin C, sodium bisulfite, sodium thiosulfate, sodium metabisulfite, and other amino acids 1-cysteine.

The compositions can be used for injection, preferably intramuscular or subcutaneous injection, and intramuscular injection is more preferred. The composition can also be used for aerosol administration. Single-dose or multi-dose type is the usual type of the composition; its single-dose contains 3-500 mg of DEA as usual, preferably 10-200 mg. The composition could be prepared to injection or lyophilized preparations, and the latter is preferred.

The injectable suspension of the composition contains 0.3-25% (w/v) of BEA, 0.01-5% (w/v) of surfactant, preferably 0.1-1% (w/v); 0.01-3% (w/v) of suspending agent, preferably 0.05-0.8% (w/v); it also contains osmotic pressure regulator, preferably sodium chloride or dextrose.

The lyophilized formulation of the composition can be used for clinic after diluting with sterile water for injection, which contains 3-500 mg of BEA particles, preferably 10-200 mg. The ratio of BEA particles and surfactants is 1:50-500:1, preferably 1:5-100:1. The ratio of BEA particles and suspending agents is 0.1:10-500:1, preferably 1:5-100:1. The composition contains one lyophilization protectant at least.

The present invention also provides three methods for the preparation of the composition. The first method has the steps of (a) dissolving the BEA in the right amount of solvent, adding water, recrystallizing it and remove the solvent after that; (b) preparing the excipients solution with dissolving each of the excipients in water; (c) dispersing the recrystallized BEA in the excipients solution; (d) homogenizing in high pressure; and (e) filling and sealing; or filling, lyophilizing and sealing.

The second method has the steps of (a) preparing the excipient solution through dissolving each of the excipients in water; (b) dispersing the BEA in the excipients solution; (c) homogenize in high pressure; and (d) filling and sealing; or filling, lyophilizing and sealing.

The third method has the steps of (a) preparing the excipient solution through dissolving each of the excipients in water; (b) dispersing BEA particles in the excipients solution and mixing continuously until it is wetted sufficiently; (c) filling and sealing; or filling, lyophilizing and sealing.

Example 1. Preparation of Formulations and Compositions

The following Formulation/Compositions are provided to explain the present invention, and to describe the materials and methods used in the preparation of injectable formulations and compositions containing 16alpha-bromo-3beta-hydroxy-5alpha-androstan-17-ketone or its hydrates (BEA). The Formulation/Compositions should by no means be interpreted as defining the scope of the present invention.

The BEA particles are prepared in 2 methods. In the first method, 500 g of BEA hemihydrate is dissolved in 10 L of anhydrous ethanol; 40 L of water is added to the solution while stirring; a white powder is precipitated, filtered, washed with water, and dried to get BEA Particles I (467 g). In the second method, 100 g of BEA hemihydrate is micronized twice with jet-milling micronizer to get BEA Particles II (87 g).

Formulation of Composition 1 (100 Vials):

| Ingredient | Amount (g) |
| --- | --- |
| BEA Particles | 5 |
| Poloxamer 188 | 0.5 |
| Carboxymethylcellulose Sodium | 0.4 |
| Sodium Dihydrogen Phosphate | 0.14 |
| Sodium Hydroxide | As needed |
| Mannitol | 5 |

Method of preparation: excipients is added thereto to dissolve in 70 mL of water, and the pH of the solution is adjusted to about 7; BEA Particles I is dispersed in the solution obtained and then water is added to adjust the total volume to 100 mL; the solution is homogenized 2 times with the pressure of 600 bar by high-pressure homogenizer. And the resultant preparation solution (1 mL) is filled into ampoules, respectively, followed by lyophilization.

Formulation of Composition 2 (100 Vials):

| Ingredient | Amount(g) |
| --- | --- |
| BEA Particles | 5 |
| Twain 80 | 0.5 |
| Carboxymethylcellulose Sodium | 0.4 |
| Sodium Dihydrogen Phosphate | 0.14 |
| Sodium Hydroxide | As needed |
| Mannitol | 5 |

Method of preparation: excipients is added thereto to dissolve in 70 mL of water, and the pH of the solution is adjusted to about 7; BEA Particles I is dispersed in the solution obtained and then water is added to adjust the total volume to 100 mL; the solution is homogenized 2 times with the pressure of 600 bar by high-pressure homogenizer. And the resultant preparation solution (1 mL) is filled into ampoules, respectively, and then followed by lyophilization.

Formulation of Composition 3 (100 Vials):

| Ingredient | Amount(g) |
| --- | --- |
| BEA Particles | 5 |
| Polyethylene Glycol Hydroxystearate | 0.5 |
| Carboxymethylcellulose Sodium | 0.4 |
| Sodium Dihydrogen Phosphate | 0.14 |
| Sodium Hydroxide | As needed |
| Mannitol | 5 |

Method of preparation: excipients is added thereto to dissolve in 70 mL of water, and the pH of the solution is adjusted to about 7; BEA Particles I is dispersed in the solution obtained and then water is added to adjust the total volume to 100 mL; the solution is homogenized 2 times with the pressure of 600 bar by high-pressure homogenizer. And the resultant preparation solution (1 mL) is filled into ampoules, respectively, and then followed by lyophilization.

Formulation of Composition 4 (100 Vials):

| Ingredient | Amount(g) |
| --- | --- |
| BEA Particles | 5 |
| Poloxamer 188 | 0.5 |
| Carboxymethylcellulose Sodium | 0.4 |
| Sodium Dihydrogen Phosphate | 0.14 |
| Sodium Hydroxide | As needed |
| Glucose | 5 |

Method of preparation: excipients is added thereto to dissolve in 70 mL of water, and the pH of the solution is adjusted to about 7; BEA Particles I is dispersed in the solution obtained and then water is added to adjust the total volume to 100 mL; the solution is homogenized 2 times with the pressure of 600 bar by high-pressure homogenizer. And the resultant preparation solution (1 mL) is filled into ampoules, respectively, and then sterilized at 117° C. for 30 min after sealed.

Formulation of Composition 5 (100 Vials):

| Ingredient | Amount(g) |
| --- | --- |
| BEA Particles | 5 |
| Twain 80 | 0.5 |
| Carboxymethylcellulose Sodium | 0.4 |
| Sodium Dihydrogen Phosphate | 0.14 |
| Sodium Hydroxide | As needed |
| Glucose | 5 |

Method of preparation: excipients is added thereto to dissolve in 70 mL of water, and the pH of the solution is adjusted to about 7; BEA Particles I is dispersed in the solution obtained and then water is added to adjust the total volume to 100 mL; the solution is homogenized 2 times with the pressure of 600 bar by high-pressure homogenizer. And the resultant preparation solution (1 mL) is filled into ampoules, respectively, and then sterilized at 117° C. for 30 min after sealed.

Formulation of Composition 6 (100 Vials):

| Ingredient | Amount(g) |
| --- | --- |
| BEA Particles | 5 |
| Polyethylene Glycol Hydroxystearate | 0.5 |
| Carboxymethylcellulose Sodium | 0.4 |
| Sodium Dihydrogen Phosphate | 0.14 |
| Sodium Hydroxide | As needed |
| Glucose | 5 |

Method of preparation: excipients is added thereto to dissolve in 70 mL of water, and the pH of the solution is adjusted to about 7; BEA Particles I is dispersed in the solution obtained and then water is added to adjust the total volume to 100 mL; the solution is homogenized 2 times with the pressure of 600 bar by high-pressure homogenizer. And the resultant preparation solution (1 mL) is filled into ampoules, respectively, and then sterilized at 117° C. for 30 min after sealed.

Formulation of Composition 7 (100 Vials):

| Ingredient | Amount(g) |
| --- | --- |
| BEA Particles | 0.3 |
| Poloxamer 188 | 5 |
| Carboxymethylcellulose Sodium | 0.01 |
| Sodium Acetate | 0.1 |
| Hydrochloric Acid | As needed |
| Sorbitol | 5 |

Method of preparation: excipients are dissolved in about 70 mL of water, and the pH of the solution is adjusted with HCl to about 7; BEA Particles I is dispersed in the solution obtained and then water is added to adjust the total volume to 100 mL; the solution is homogenized 4 times with the pressure of 600 bar by high-pressure homogenizer. And the resultant preparation solution (1 mL) is filled into ampoules, respectively, and then followed by lyophilization.

Formulation of Composition 8 (100 Vials):

| Ingredient | Amount(g) |
| --- | --- |
| BEA Particles | 50 |
| Poloxamer 188 | 0.1 |
| Carboxymethylcellulose Sodium | 0.5 |
| Glucose | 5 |

Method of preparation: excipients are dissolved in about 160 mL of water; BEA Particles I is dispersed in the solution obtained with stirring and then water is added to adjust the total volume to 200 mL; the solution (2 mL) is filled into ampoules, respectively, and followed by lyophilization.

Formulation of Composition 9 (100 Vials):

| Ingredient | Amount(g) |
| --- | --- |
| BEA Particles | 1 |
| Poloxamer 188 | 5 |
| Polyethylene Glycol 3350 | 1.5 |
| Sodium Dihydrogen Phosphate | 0.1 |
| Sodium Hydroxide | As needed |
| Phenol | 0.5 |
| Mannitol | 5 |

Method of Preparation: Excipients are Dissolved in about 80 mL of Water, and the pH of the solution is adjusted with NaOH to about 6; BEA Particles I is dispersed in the solution obtained and then water is added to adjust the total volume to 100 mL; the solution is homogenized 4 times with the pressure of 600 bar by high-pressure homogenizer. And the resultant preparation solution (1 mL) is filled into ampoules, respectively, and then followed by lyophilization.

Formulation of Composition 10 (100 Vials):

| Ingredient | Amount(g) |
| --- | --- |
| BEA Particles | 1 |
| Poloxamer 188 | 0.01 |
| Polyethylene Glycol 3350 | 0.03 |
| Chlorobutanol | 0.5 |
| Sucrose | 5 |

Method of preparation: excipients are dissolved in about 80 mL of water; BEA Particles I is dispersed in the solution obtained with stirring and then water is added to adjust the total volume to 100 mL; the solution (1 mL) is filled into ampoules, respectively, and followed by lyophilization.

Formulation of Composition 11 (100 Vials):

| Ingredient | Amount(g) |
| --- | --- |
| BEA Particles | 10 |
| Poloxamer 188 | 0.2 |
| Carboxymethylcellulose Sodium | 0.6 |
| Sodium Dihydrogen Phosphate | 0.2 |
| Sodium Hydroxide, Hydrochloric Acid | As needed |
| Mannitol | 5 |

Method of preparation: excipients are dissolved in about 80 mL of water, and the pH of the solution is adjusted with NaOH and HCl to about 5; BEA Particles I is dispersed in the solution obtained and then water is added to adjust the total volume to 100 mL; the solution is homogenized 4 times with the pressure of 600 bar by high-pressure homogenizer. And the resultant preparation solution (1 mL) is filled into ampoules, respectively, and then followed by lyophilization.

Formulation of the Composition 12 (100 Vials):

| Ingredient | Amount(g) |
| --- | --- |
| BEA Particles | 20 |
| Poloxamer 188 | 1 |
| Polyethylene Glycol 3350 | 0.4 |
| Ethylenediaminetetraacetic Acid Calcium Disodium | 0.05 |
| Sucrose | 5 |

Method of preparation: excipients are dissolved in about 160 mL of water; BEA Particles I is dispersed in the solution obtained with stirring and then water is added to adjust the total volume to 200 mL; the solution (2 mL) is filled into ampoules, respectively, and then followed by lyophilization.

Formulation of Composition 13 (100 Vials):

| Ingredient | Amount(g) |
| --- | --- |
| BEA Particles | 5 |
| Poloxamer 188 | 0.5 |
| Carboxymethylcellulose Sodium | 0.5 |
| Sodium Dihydrogen Phosphate | 0.05 |
| Sodium Hydroxide | As needed |
| Glucose | 5 |

Method of preparation: excipients are dissolved in about 70 mL of water, and the pH of the solution is adjusted with NaOH to about 6; BEA Particles I is dispersed in the solution obtained and then water is added to adjust the total volume to 100 mL; the solution is homogenized 2 times with the pressure of 600 bar by high-pressure homogenizer. And the resultant preparation solution (1 mL) is filled into ampoules, respectively, followed by lyophilization.

Formulation of Composition 14 (100 Vials):

| Ingredient | Amount(g) |
| --- | --- |
| BEA Particles | 0.3 |
| Twain 80 | 1 |
| Polyethylene Glycol 1500 | 3 |
| Citric Acid | 0.1 |
| Sodium Hydroxide | As needed |
| Sorbitol | 5 |

Method of preparation: Excipients are dissolved in about 70 mL of water, and the pH of the solution is adjusted with NaOH to about 6; BEA Particles I is dispersed in the solution obtained and then water is added to adjust the total volume to 100 mL; The solution is homogenized 2 times with the pressure of 600 bar by high-pressure homogenizer. And the resultant preparation solution (1 mL) is filled into ampoules, respectively, followed by lyophilization.

Formulation of Composition 15 (100 Vials):

| Ingredient | Amount(g) |
| --- | --- |
| BEA Particles | 50 |
| Twain 80 | 3 |
| Carboxymethylcellulose Sodium | 0.1 |
| Glucose | 5 |

Method of preparation: excipients are dissolved in about 150 mL of water; BEA Particles I is dispersed in the solution obtained with stirring and then water is added to adjust the total volume to 200 mL; the solution (2 mL) is filled into ampoules, respectively, and followed by lyophilization.

Formulation/Composition 16 (100 Vials):

| Ingredient | Amount(g) |
| --- | --- |
| BEA Particles | 1 |
| Twain 80 | 0.1 |

-continued

| Ingredient | Amount(g) |
|---|---|
| Carboxymethylcellulose Sodium | 0.1 |
| Sodium Dihydrogen Phosphate | 0.1 |
| Sodium Hydroxide | As needed |
| Sorbitol | 5 |

Method of preparation: excipients are dissolved in about 70 mL of water, and the pH of the solution is adjusted with NaOH to about 6; BEA Particles I is dispersed in the solution obtained and then water is added to adjust the total volume to 100 mL; the solution is homogenized 2 times with the pressure of 600 bar by high-pressure homogenizer. And the resultant preparation solution (1 mL) is filled into ampoules, respectively, followed by lyophilization.
Formulation/Composition 17 (100 Vials):

| Ingredient | Amount(g) |
|---|---|
| BEA Particles | 20 |
| Twain 80 | 0.1 |
| Carboxymethylcellulose Sodium | 0.3 |
| Glucose | 5 |

Method of preparation: excipients are dissolved in about 160 mL of water; BEA Particles I is dispersed in the solution obtained with stirring and then water is added to adjust the total volume to 200 mL; the solution (2 mL) is filled into ampoules, respectively, and followed by lyophilization.
Formulation of Composition 18 (100 Vials):

| Ingredient | Amount(g) |
|---|---|
| BEA Particles | 2 |
| Twain 80 | 0.2 |
| Carboxymethylcellulose Sodium | 0.7 |
| Sodium Dihydrogen Phosphate | 0.3 |
| Sodium Hydroxide | As needed |
| Phenol | 0.5 |
| Mannitol | 5 |

Method of preparation: excipients are dissolved in about 80 mL of water, and the pH of the solution is adjusted with NaOH to about 6; BEA Particles I is dispersed in the solution obtained and then water is added to adjust the total volume to 100 mL; the solution is homogenized 2 times with the pressure of 800 bar by high-pressure homogenizer. And the resultant preparation solution (1 mL) is filled into ampoules, respectively, and then followed by lyophilization.
Formulation of Composition 19 (100 Vials):

| Ingredient | Amount(g) |
|---|---|
| BEA Particles | 10 |
| Twain 80 | 0.6 |
| Carboxymethylcellulose Sodium | 0.2 |
| Sodium Dihydrogen Phosphate | 0.02 |
| Sodium Hydroxide | As needed |
| Mannitol | 5 |

Method of preparation: excipients are dissolved in about 80 mL of water, and the pH of the solution is adjusted with NaOH to about 6; BEA Particles I is dispersed in the solution obtained and then water is added to adjust the total volume to 100 mL; the solution is homogenized 2 times with the pressure of 400 bar by high-pressure homogenizer. And the resultant preparation solution (1 mL) is filled into ampoules, respectively, and then followed by lyophilization.
Formulation of Composition 20 (100 Vials):

| Ingredient | Amount(g) |
|---|---|
| BEA Particles | 5 |
| Twain 80 | 1.2 |
| Carboxymethylcellulose Sodium | 0.5 |
| Sodium Dihydrogen Phosphate | 0.1 |
| Sodium Hydroxide | As needed |
| Mannitol | 5 |

Method of preparation: excipients are dissolved in about 70 mL of water, and the pH of the solution is adjusted with NaOH to about 6; BEA Particles I is dispersed in the solution obtained and then water is added to adjust the total volume to 100 mL; the solution is homogenized 2 times with the pressure of 600 bar by high-pressure homogenizer. And the resultant preparation solution (1 mL) is filled into ampoules, respectively, followed by lyophilization.
Formulation of Composition 21 (100 Vials):

| Ingredient | Amount(g) |
|---|---|
| BEA Particles | 0.3 |
| Polyethylene Glycol Hydroxystearate | 0.01 |
| Polyethylene Glycol 1500 | 1.5 |
| Sodium Dihydrogen Phosphate | 0.1 |
| Sodium Hydroxide | As needed |
| Ethylenediaminetetraacetic Acid Calcium Disodium | 0.05 |
| Sorbitol | 5 |

Method of preparation: excipients are dissolved in about 70 mL of water, and the pH of the solution is adjusted with NaOH to about 6; BEA Particles I is dispersed in the solution obtained and then water is added to adjust the total volume to 100 mL; the solution is homogenized 2 times with the pressure of 600 bar by high-pressure homogenizer. And the resultant preparation solution (1 mL) is filled into ampoules, respectively, and followed by lyophilization.
Formulation of Composition 22 (100 Vials):

| Ingredient | Amount(g) |
|---|---|
| BEA Particles | 50 |
| Polyethylene Glycol Hydroxystearate | 10 |
| Carboxymethylcellulose Sodium | 0.5 |
| Glucose | 5 |

Method of preparation: excipients are dissolved in about 160 mL of water; BEA Particles I is dispersed in the solution obtained with stirring and then water is added to adjust the total volume to 200 mL; the solution (2 mL) is filled into ampoules, respectively, and followed by lyophilization.
Formulation of Composition 23 (100 Vials):

| Ingredient | Amount(g) |
|---|---|
| BEA Particles | 1 |
| Polyethylene Glycol Hydroxystearate | 0.1 |
| Carboxymethylcellulose Sodium | 1.2 |
| Sodium Acetate | 0.1 |
| Hydrochloric Acid | As needed |
| Sorbitol | 5 |

Method of preparation: excipients are dissolved in about 70 mL of water, and the pH of the solution is adjusted with NaOH to about 6; BEA Particles I is dispersed in the solution obtained and then water is added to adjust the total volume to 100 mL; the solution is homogenized 2 times with the pressure of 600 bar by high-pressure homogenizer. And the resultant preparation solution (1 mL) is filled into ampoules, respectively, and followed by lyophilization.

Formulation of Composition 24 (100 Vials):

| Ingredient | Amount(g) |
|---|---|
| BEA Particles | 15 |
| Polyethylene Glycol Hydroxystearate | 2.5 |
| Carboxymethylcellulose Sodium | 0.9 |
| Glucose | 5 |

Method of preparation: excipients are dissolved in about 160 mL of water; BEA Particles I is dispersed in the solution obtained with stirring and then water is added to adjust the total volume to 200 mL; the solution (2 mL) is filled into ampoules, respectively, and followed by lyophilization.

Formulation of Composition 25 (100 Vials):

| Ingredient | Amount(g) |
|---|---|
| BEA Particles | 5 |
| Polyethylene Glycol Hydroxystearate | 0.2 |
| Carboxymethylcellulose Sodium | 1 |
| Sodium Dihydrogen Phosphate | 0.1 |
| Sodium Hydroxide | As needed |
| Phenol | 0.5 |
| Mannitol | 5 |

Method of preparation: excipients are dissolved in about 80 mL of water, and the pH of the solution is adjusted with NaOH to about 6; BEA Particles I is dispersed in the solution obtained and then water is added to adjust the total volume to 100 mL; the solution is homogenized 2 times with the pressure of 800 bar by high-pressure homogenizer. And the resultant preparation solution (1 mL) is filled into ampoules, respectively, and then followed by lyophilization.

Formulation of Composition 26 (100 Vials):

| Ingredient | Amount(g) |
|---|---|
| BEA Particles | 10 |
| Polyethylene Glycol Hydroxystearate | 1 |
| Carboxymethylcellulose Sodium | 0.5 |
| Sodium Dihydrogen Phosphate | 0.08 |
| Sodium Hydroxide | As needed |
| Mannitol | 5 |

Method of preparation: excipients are dissolved in about 80 mL of water, and the pH of the solution is adjusted with NaOH to about 6; BEA Particles I is dispersed in the solution obtained and then water is added to adjust the total volume to 100 mL; the solution is homogenized 2 times with the pressure of 400 bar by high-pressure homogenizer. And the resultant preparation solution (1 mL) is filled into ampoules, respectively, and then followed by lyophilization.

Formulation of Composition 27 (100 Vials):

| Ingredient | Amount(g) |
|---|---|
| BEA Particles | 2 |
| Polyethylene Glycol Hydroxystearate | 2 |
| Carboxymethylcellulose Sodium | 0.8 |
| Sodium Dihydrogen Phosphate | 0.1 |
| Sodium Hydroxide | As needed |
| Mannitol | 5 |

Method of preparation: excipients are dissolved in about 70 mL of water, and the pH of the solution is adjusted with NaOH to about 6; BEA Particles I is dispersed in the solution obtained and then water is added to adjust the total volume to 100 mL; the solution is homogenized 2 times with the pressure of 600 bar by high-pressure homogenizer. And the resultant preparation solution (1 mL) is filled into ampoules, respectively, and followed by lyophilization.

Formulation of Composition 28 (100 Vials):

| Ingredient | Amount(g) |
|---|---|
| BEA Particles | 3 |
| Poloxamer 188 | 0.01 |
| Sodium Acetate | 0.1 |
| Hydrochloric Acid | As needed |
| Sodium Chloride | 0.9 |

Method of preparation: excipients are dissolved in about 70 mL of water, and the pH of the solution is adjusted with HCl to about 7; BEA Particles I is dispersed in the solution obtained and then water is added to adjust the total volume to 100 mL; the solution is homogenized 4 times with the pressure of 600 bar by high-pressure homogenizer. And the resultant preparation solution (1 mL) is filled into ampoules, respectively, and then sterilized at 117° C. for 30 min after sealed.

Formulation of Composition 29 (100 Vials):

| Ingredient | Amount(g) |
|---|---|
| BEA Particles | 50 |
| Poloxamer 188 | 10 |
| Carboxymethylcellulose Sodium | 0.5 |
| Glucose | 5 |

Method of preparation: excipients are dissolved in about 160 mL of water; BEA Particles I is dispersed in the solution obtained with stirring and then water is added to adjust the total volume to 200 mL; the solution (2 mL) is filled into ampoules, respectively, and then sterilized at 117° C. for 30 min after sealed.

Formulation of Composition 30 (100 Vials):

| Ingredient | Amount(g) |
|---|---|
| BEA Particles | 0.3 |
| Poloxamer 188 | 0.1 |
| Polyethylene Glycol 3350 | 1.5 |
| Sodium Dihydrogen Phosphate | 0.2 |
| Sodium Hydroxide | As needed |
| Phenol | 0.5 |
| Sodium Chloride | 0.9 |

Method of preparation: excipients are dissolved in about 80 mL of water, and the pH of the solution is adjusted with NaOH to about 6; BEA Particles I is dispersed in the solution obtained and then water is added to adjust the total volume to 100 mL; the solution is homogenized 4 times with the pressure of 600 bar by high-pressure homogenizer. And the resultant preparation solution (1 mL) is filled into ampoules, respectively, and then sterilized at 117° C. for 30 min after sealed.

Formulation of Composition 31 (100 Vials):

| Ingredient | Amount(g) |
|---|---|
| BEA Particles | 20 |
| Poloxamer 188 | 1 |
| Polyethylene Glycol 3350 | 0.8 |
| Sodium Chloride | 0.9 |

Method of preparation: excipients are dissolved in about 70 mL of water; BEA Particles I is dispersed in the solution obtained with stirring and then water is added to adjust the total volume to 100 mL; the solution (1 mL) is filled into ampoules, respectively, and then sterilized at 117° C. for 30 min after sealed.

Formulation of Composition 32 (100 Vials):

| Ingredient | Amount(g) |
|---|---|
| BEA Particles | 2.5 |
| Poloxamer 188 | 0.2 |
| Carboxymethylcellulose Sodium | 0.6 |
| Sodium Dihydrogen Phosphate | 0.2 |
| Sodium Chloride | 0.9 |
| Sodium Hydroxide, Hydrochloric Acid | As needed |
| Glucose | 5 |

Method of preparation: excipients are dissolved in about 70 mL of water, and the pH of the solution is adjusted with NaOH and HCl to about 5; BEA Particles I is dispersed in the solution obtained and then water is added to adjust the total volume to 100 mL; the solution is homogenized 4 times with the pressure of 600 bar by high-pressure homogenizer. And the resultant preparation solution (1 mL) is filled into ampoules, respectively, and then sterilized at 117° C. for 30 min after sealed.

Formulation of Composition 33 (100 Vials):

| Ingredient | Amount(g) |
|---|---|
| BEA Particles | 7.5 |
| Poloxamer 188 | 0.8 |
| Polyethylene Glycol 3350 | 0.6 |
| Sodium Chloride | 5 |

Method of preparation: excipients are dissolved in about 80 mL of water; BEA Particles I is dispersed in the solution obtained with stirring and then water is added to adjust the total volume to 100 mL; the solution (1 mL) is filled into ampoules, respectively, and then sterilized at 117° C. for 30 min after sealed.

Formulation of Composition 34 (100 Vials):

| Ingredient | Amount(g) |
|---|---|
| BEA Particles | 5 |
| Poloxamer 407 | 2.5 |
| Carboxymethylcellulose Sodium | 0.5 |
| Sodium Dihydrogen Phosphate | 0.05 |
| Sodium Hydroxide | As needed |
| Glucose | 5 |

Method of preparation: excipients are dissolved in about 70 mL of water, and the pH of the solution is adjusted with NaOH to about 6; BEA Particles I is dispersed in the solution obtained and then water is added to adjust the total volume to 100 mL; the solution is homogenized 2 times with the pressure of 600 bar by high-pressure homogenizer. And the resultant preparation solution (1 mL) is filled into ampoules, respectively, and then sterilized at 121° C. for 8 min after sealed.

Formulation of Composition 35 (100 Vials):

| Ingredient | Amount(g) |
|---|---|
| BEA Particles | 0.3 |
| Twain 80 | 0.01 |
| Polyethylene Glycol 1500 | 0.05 |
| Sodium Dihydrogen Phosphate | 0.1 |
| Sodium Hydroxide | As needed |
| Glycerin | 2 |

Method of preparation: excipients are dissolved in about 70 mL of water, and the pH of the solution is adjusted with NaOH to about 6; BEA Particles I is dispersed in the solution obtained and then water is added to adjust the total volume to 100 mL; the solution is homogenized 2 times with the pressure of 600 bar by high-pressure homogenizer. And the resultant preparation solution (1 mL) is filled into ampoules, respectively, and then sterilized at 117° C. for 25 min after sealed.

Formulation of Composition 36 (100 Vials):

| Ingredient | Amount(g) |
|---|---|
| BEA Particles | 50 |
| Twain 80 | 3 |
| Carboxymethylcellulose Sodium | 0.2 |
| Glucose | 5 |

Method of preparation: excipients are dissolved in about 150 mL of water; BEA Particles I is dispersed in the solution obtained with stirring and then water is added to adjust the total volume to 200 mL; the solution (2 mL) is filled into ampoules, respectively, and then sterilized at 117° C. for 30 min after sealed.

Formulation of Composition 37 (100 Vials):

| Ingredient | Amount(g) |
|---|---|
| BEA Particles | 1 |
| Twain 80 | 0.1 |
| Poloxamer 188 | 0.1 |
| Carboxymethylcellulose Sodium | 0.1 |
| Sodium Dihydrogen Phosphate | 0.1 |
| Sodium Hydroxide | As needed |
| Sodium Bisulfite | 0.1 |
| Glucose | 5 |

Method of preparation: excipients are dissolved in about 70 mL of water, and the pH of the solution is adjusted with NaOH to about 6; BEA Particles I is dispersed in the solution obtained and then water is added to adjust the total volume to 100 mL; the solution is homogenized 2 times with the pressure of 600 bar by high-pressure homogenizer. And the resultant preparation solution (1 mL) is filled into ampoules, respectively, and then sterilized at 117° C. for 30 min after sealed.

Formulation of Composition 38 (100 Vials):

| Ingredient | Amount(g) |
| --- | --- |
| BEA Particles | 20 |
| Twain 80 | 1 |
| Carboxymethylcellulose Sodium | 0.3 |
| Glucose | 10 |

Method of preparation: excipients are dissolved in about 160 mL of water; BEA Particles I is dispersed in the solution obtained with stirring and then water is added to adjust the total volume to 200 mL; the solution (2 mL) is filled into ampoules, respectively, and then sterilized at 117° C. for 30 min after sealed.

Formulation of Composition 39 (100 Vials):

| Ingredient | Amount(g) |
| --- | --- |
| BEA Particles | 4 |
| Twain 80 | 0.2 |
| Carboxymethylcellulose Sodium | 0.7 |
| Sodium Dihydrogen Phosphate | 0.3 |
| Sodium Hydroxide | As needed |
| Phenol | 0.5 |
| Glucose | 5 |

Method of preparation: excipients are dissolved in about 80 mL of water, and the pH of the solution is adjusted with NaOH to about 6; BEA Particles I is dispersed in the solution obtained and then water is added to adjust the total volume to 100 mL; the solution is homogenized 2 times with the pressure of 800 bar by high-pressure homogenizer. And the resultant preparation solution (1 mL) is filled into ampoules, respectively, followed by lyophilization.

Formulation of Composition 40 (100 Vials):

| Ingredient | Amount(g) |
| --- | --- |
| BEA Particles | 10 |
| Twain 80 | 0.6 |
| Carboxymethylcellulose Sodium | 0.2 |
| Sodium Dihydrogen Phosphate | 0.02 |
| Sodium Hydroxide | As needed |
| Sodium Bisulfite | 0.1 |
| Glucose | 5 |

Method of preparation: excipients are dissolved in about 80 mL of water, and the pH of the solution is adjusted with NaOH to about 6; BEA Particles I is dispersed in the solution obtained and then water is added to adjust the total volume to 100 mL; the solution is homogenized 2 times with the pressure of 400 bar by high-pressure homogenizer. And the resultant preparation solution (1 mL) is filled into ampoules, respectively, and then sterilized at 117° C. for 30 min after sealed.

Formulation of Composition 41 (100 Vials):

| Ingredient | Amount(g) |
| --- | --- |
| BEA Particles | 5 |
| Twain 80 | 1.2 |
| Carboxymethylcellulose Sodium | 0.5 |
| Citric Acid | 0.1 |
| Sodium Hydroxide | As needed |
| Glucose | 5 |

Method of preparation: excipients are dissolved in about 70 mL of water, and the pH of the solution is adjusted with NaOH to about 6; BEA Particles I is dispersed in the solution obtained and then water is added to adjust the total volume to 100 mL; the solution is homogenized 2 times with the pressure of 600 bar by high-pressure homogenizer. And the resultant preparation solution (1 mL) is filled into ampoules, respectively, and then sterilized at 117° C. for 30 min after sealed.

Formulation of Composition 42 (100 Vials):

| Ingredient | Amount(g) |
| --- | --- |
| BEA Particles | 0.3 |
| Polyethylene Glycol Hydroxystearate | 0.01 |
| Polyethylene Glycol 1500 | 0.08 |
| Sodium Dihydrogen Phosphate | 0.1 |
| Sodium Hydroxide | As needed |
| Ethylenediaminetetraacetic Acid Calcium Disodium | 0.05 |
| Glucose | 5 |

Method of preparation: excipients are dissolved in about 70 mL of water, and the pH of the solution is adjusted with NaOH to about 6; BEA Particles I is dispersed in the solution obtained and then water is added to adjust the total volume to 100 mL; the solution is homogenized 2 times with the pressure of 600 bar by high-pressure homogenizer. And the resultant preparation solution (1 mL) is filled into ampoules, respectively, and then sterilized at 117° C. for 30 min after sealed.

Formulation of Composition 43 (100 Vials):

| Ingredient | Amount(g) |
| --- | --- |
| BEA Particles | 50 |
| Polyethylene Glycol Hydroxystearate | 10 |
| Carboxymethylcellulose Sodium | 0.5 |
| Glucose | 5 |

Method of preparation: excipients are dissolved in about 160 mL of water; BEA Particles I is dispersed in the solution obtained with stirring and then water is added to adjust the total volume to 200 mL; the solution (2 mL) is filled into ampoules, respectively, and then sterilized at 117° C. for 30 min after sealed.

Formulation of Composition 44 (100 Vials):

| Ingredient | Amount(g) |
| --- | --- |
| BEA Particles | 1 |
| Polyethylene Glycol Hydroxystearate | 0.1 |
| Carboxymethylcellulose Sodium | 3 |
| Sodium Acetate | 0.1 |
| Hydrochloric Acid | As needed |
| Glucose | 5 |

Method of preparation: excipients are dissolved in about 70 mL of water, and the pH of the solution is adjusted with NaOH to about 6; BEA Particles I is dispersed in the solution obtained and then water is added to adjust the total volume to 100 mL; the solution is homogenized 2 times with the pressure of 600 bar by high-pressure homogenizer. And the resultant preparation solution (1 mL) is filled into ampoules, respectively, and then sterilized at 117° C. for 30 min after sealed.

Formulation of Composition 45 (100 Vials):

| Ingredient | Amount(g) |
| --- | --- |
| BEA Particles | 15 |
| Polyethylene Glycol Hydroxystearate | 2.5 |
| Carboxymethylcellulose Sodium | 0.9 |
| Glucose | 9 |

Method of preparation: excipients are dissolved in about 160 mL of water; BEA Particles I is dispersed in the solution obtained with stirring and then water is added to adjust the total volume to 200 mL; the solution (2 mL) is filled into ampoules, respectively, and then sterilized at 117° C. for 30 min after sealed.

Formulation of Composition 46 (100 Vials):

| Ingredient | Amount(g) |
| --- | --- |
| BEA Particles | 5 |
| Polyethylene Glycol Hydroxystearate | 0.2 |
| Carboxymethylcellulose Sodium | 1 |
| Sodium Dihydrogen Phosphate | 0.1 |
| Sodium Hydroxide | As needed |
| Phenol | 0.5 |
| Glucose | 5 |

Method of preparation: excipients are dissolved in about 70 mL of water, and the pH of the solution is adjusted with NaOH to about 6; BEA Particles I is dispersed in the solution obtained and then water is added to adjust the total volume to 100 mL; the solution is homogenized 2 times with the pressure of 800 bar by high-pressure homogenizer. And the resultant preparation solution (1 mL) is filled into ampoules, respectively, and then sterilized at 117° C. for 30 min after sealed.

Formulation of Composition 47 (100 Vials):

| Ingredient | Amount(g) |
| --- | --- |
| BEA Particles | 6 |
| Polyethylene Glycol Hydroxystearate | 1 |
| Carboxymethylcellulose Sodium | 0.5 |
| Sodium Dihydrogen Phosphate | 0.08 |
| Sodium Hydroxide | As needed |
| Glucose | 5 |

Method of preparation: excipients are dissolved in about 80 mL of water, and the pH of the solution is adjusted with NaOH to about 6; BEA Particles I is dispersed in the solution obtained and then water is added to adjust the total volume to 100 mL; the solution is homogenized 2 times with the pressure of 400 bar by high-pressure homogenizer. And the resultant preparation solution (1 mL) is filled into ampoules, respectively, and then sterilized at 117° C. for 30 min after sealed.

Formulation of Composition 48 (100 Vials):

| Ingredient | Amount(g) |
| --- | --- |
| BEA Particles | 5 |
| Polyethylene Glycol Hydroxystearate | 2.5 |
| Carboxymethylcellulose Sodium | 0.8 |
| Sodium Dihydrogen Phosphate | 0.1 |
| Sodium Hydroxide | As needed |
| Glucose | 5 |

Method of preparation: excipients are dissolved in about 70 mL of water, and the pH of the solution is adjusted with NaOH to about 6; BEA Particles I is dispersed in the solution obtained and then water is added to adjust the total volume to 100 mL; the solution is homogenized 2 times with the pressure of 600 bar by high-pressure homogenizer. And the resultant preparation solution (1 mL) is filled into ampoules, respectively, and then sterilized at 117° C. for 30 min after sealed.

Example 2. Stability Test of Formulation and Composition

The Formulations of Compositions 1-6 of the present invention and Example 1 of US20030060425A1 are stored at 60° C. for 10 days and 40° C.±2° C., RH75%±5% for 30 days, respectively. Samples of the preparations are taken to analyze their BEA and related substances (degradation products) concentration.

The conditions for the analysis are as follow: Chromatographic Conditions of HPLC: High Performance Liquid Chromatograph: Waters-e2685; Mobile Phase: Acetonitrile-water (60/40); Chromatographic Column: C18, 4.6×250 mm;

Detector: UV; Wavelength: 210 nm; Sample Size: 201; Flow Rate: 1.2 ml/min; Column Temperature: Room Temperature.

Determination of BEA Content: The stock solution of reference substance (BEA standard) is made and diluted with the mobile phase to make standard solutions. The solutions are analyzed to make the standard curves. The samples are dissolved and diluted with the mobile phase to make the BEA concentration at about 1 mg/mL. The samples are then analyzed and the concentrations of BEA are calculated based on external standard curve.

Determination of related substances (degradation products): the test solution is prepared in accordance with the method described in Determination of BEA Content. The solutions are analyzed and the content of related substances are calculated based on their relative concentrations to BEA.

TABLE 2-1

Stability of Invention Formulation/Composition and Existing Formulation

| Samples | 0 day BEA (%) | 0 day related reference (%) | 60° C. 10 days BEA (%) | 60° C. 10 days related reference (%) | 40° C. 30 days BEA (%) | 40° C. 30 days related reference (%) |
|---|---|---|---|---|---|---|
| Formulation/Composition 1 | 95.1 | 0.35 | 95.5 | 0.50 | 94.8 | 0.40 |
| Formulation/Composition 2 | 95.9 | 0.38 | 95.2 | 0.56 | 94.0 | 0.56 |
| Formulation/Composition 3 | 96.0 | 0.40 | 96.7 | 0.71 | 93.9 | 0.88 |
| Formulation/Composition 4 | 98.2 | 2.31 | 98.5 | 2.54 | 97.6 | 2.63 |
| Formulation/Composition 5 | 99.8 | 2.52 | 99.1 | 2.91 | 98.2 | 3.14 |
| Formulation/Composition 6 | 97.0 | 3.43 | 95.2 | 5.03 | 95.1 | 6.22 |
| Example 1, WO2000056757A1 | 92.1 | 8.13 | 45.0 | 53.32 | 40.8 | 55.91 |

The results indicate that the stability of Formulation/Composition 1-6 of the present invention is significantly better than that of Example 1 of WO2000056757A1. Table 2-2 summarizes the extend of degradation for 3 types of formulations.

TABLE 2-2

Comparison of the BEA Loss Between the Present Invention and Published Formulation in Degradation Studies

| Formulation Type | BEA Loss 60° C. 10 days | BEA Loss 40° C. 30 days |
|---|---|---|
| Water Dispersible BEA Composition (Composition/Formulation 1-3) | 0.1% | −1.5% |
| Aqueous BEA Formulation (Composition/Formulation 4-6) | −0.7% | −1.4% |
| Non-aqueous BEA formulation (Example 1. WO2000056757A1) | −51.1% | −55.7% |

As shown in Table 2-2, for water dispersible BEA compositions, the average change (Composition/Formulation 1-3) in BEA is 0.1% and −1.5% at 60° C. for 10 days and 40° C. for 30 days. The change for aqueous BEA formulation (Composition/Formulation 4-6) are −0.7% and −1.4%, 1.4% respectively. In comparison, the non-aqueous BEA formulation (Example 1, WO2000056757A1) in the same study, the change of BEA is −51% and −55.7%, thus, the loss of BEA in the non-aqueous BEA formulation of Example 1 of WO2000056757A1 is 34-428 folds worse than the present invention composition/formulation.

Example 3. Particle Size Determination

Samples are prepared in accordance with the formulations in Table 3-1 and the method described in Formulation of Composition 1, with Cremophor EL, lecithin, sodium oleate are used as surfactant (100 vials, 1 mL/vial, lyophilized).

TABLE 3-1

Formulations

| Formulation a | Amount(g) | Formulation b | Amount(g) | Formulation c | Amount(g) |
|---|---|---|---|---|---|
| BEA | 5 | BEA | 5 | BEA | 5 |
| Cremophor EL | 0.5 | Lecithin | 0.5 | Sodium oleate | 0.05 |
| Carboxymethyl cellulose sodium | 0.4 | Carboxymethyl cellulose sodium | 0.4 | Carboxymethyl cellulose sodium | 0.4 |
| $NaH_2PO_4$ | 0.14 | $NaH_2PO_4$ | 0.14 | $NaH_2PO_4$ | 0.14 |
| Sodium hydroxide | As needed | Sodium hydroxide | As needed | Sodium hydroxide | As needed |
| Mannitol | 5 | Mannitol | 5 | Mannitol | 5 |

One drop of every sample in Formulations of Compositions 1-6 of the present invention and the comparative Formulations of Compositions a-c (the lyophilized injectable composition of Formulation of Compositions 1-3 and Comparative Formulation of Compositions are suspended with water as required and then observed by microscope, three micro vision are detected.

TABLE 3-2

Particle Size of Invention Formulation/Composition

| Sample | Results of particle size determination |
|---|---|
| Formulation/Composition 1 | D(90) < 5 μm |
| Formulation/Composition 2 | D(90) < 10 μm |
| Formulation/Composition 3 | D(90) < 15 μm |
| Formulation/Composition 4 | D(90) < 5 μm |
| Formulation/Composition 5 | D(90) < 5 μm |
| Formulation/Composition 6 | D(90) < 10 μm |
| Comparative Formulation/Composition a | particle aggregation |
| Comparative Formulation/Composition b | particle aggregation |
| Comparative Formulation/Composition c | particle aggregation |

The particle size results indicate there is no apparent particle aggregation for Formulation/Composition 1-6, 90% of the particles are less than 15 μm. The sample using Poloxamer as Surfactant has the smallest particle size, while particle aggregation occurred in all of the comparative Formulation/Compositions.

Example 4. Injection Site Irritation Test

The samples are prepared in accordance with the formulation in Table 4-1 and the method described in Formulation of Composition 4 in Example 1. They contained 6% of Poloxamer, 2% of twain 80 and 6% of Polyoxyethylene Hydroxystearate (100 mL), respectively.

TABLE 4-1

Formulations

| Comparative Formulation/ Composition d | Amount (g) | Comparative Formulation/ Composition e | Amount (g) | Comparative Formulation/ Composition f | Amount (g) |
|---|---|---|---|---|---|
| BEA | 5 | BEA | 5 | BEA | 5 |
| Poloxamer | 6 | Twain 80 | 2 | Polyoxyethylene Hydroxystearate | 6 |
| Carboxymethylcellulose sodium | 0.4 | Carboxymethylcellulose sodium | 0.4 | Carboxymethylcellulose sodium | 0.4 |
| NaH$_2$PO$_4$ | 0.14 | NaH$_2$PO$_4$ | 0.14 | NaH$_2$PO$_4$ | 0.14 |
| Sodium hydroxide | As needed | Sodium hydroxide | As needed | Sodium hydroxide | As needed |
| Mannitol | 5 | Mannitol | 5 | Mannitol | 5 |

153 healthy rabbits are divided into 51 groups randomly, with 3 rabbits in each group. The rabbits are fixed and their hair on quadriceps on both sides is shaved off. The quadriceps muscle on the left leg of each rabbit is injected with 1 mL of the test solution after the muscle is disinfected with iodine tincture and alcohol, and the quadriceps muscle on the right leg is injected with physiological saline as reference. All of the rabbits are sacrificed 48 h after the injection. The quadriceps muscle is excised and analyzed for injection site irritation (congestion, edema, induration, degeneration or necrosis). The orders of reaction are assigned according to Table 4-2.

TABLE 4-2

Orders of Reaction

| Reaction Score | Reaction |
|---|---|
| 0 | No apparent reaction at the injection site |
| 1 | Slight congestion at the injection site, the diameter is less than 0.5 cm |
| 2 | Moderate congestion at the injection site, the diameter is less than 1.0 cm |
| 3 | Severe congestion at the injection site, red and swollen or muscle degeneration |
| 4 | Muscle degeneration or necrosis, the diameter is less than 0.5 cm |
| 5 | Severe muscle degeneration and large area of necrosis |

In general, the preparation could be used for intramuscular injection if the reaction score of the rabbits is below 2 and could not be used for intramuscular injection if the reaction score of the rabbits is beyond 3; furthermore, repeated test or consideration with other indicators could be performed if the average reaction score is between 2 and 3. Table 4-3 shows the reaction scores.

TABLE 4-3

Reaction Score of Injection Site Irritation Caused by Invention Formulation/Composition and Existing Formulation

| Sample | Average reaction order |
|---|---|
| Formulation/Composition 1 | 0 |
| Formulation/Composition 2 | 1 |
| Formulation/Composition 3 | 1 |
| Formulation/Composition 4 | 0 |
| Formulation/Composition 5 | 1 |
| Formulation/Composition 6 | 1 |

TABLE 4-3-continued

Reaction Score of Injection Site Irritation Caused by Invention Formulation/Composition and Existing Formulation

| Sample | Average reaction order |
|---|---|
| Formulation/Composition 7 | 0 |
| Formulation/Composition 8 | 1 |
| Formulation/Composition 9 | 0 |
| Formulation/Composition 10 | 0 |
| Formulation/Composition 11 | 1 |
| Formulation/Composition 12 | 1 |

TABLE 4-3-continued

Reaction Score of Injection Site Irritation Caused by Invention Formulation/Composition and Existing Formulation

| Sample | Average reaction order |
|---|---|
| Formulation/Composition 13 | 0 |
| Formulation/Composition 14 | 0 |
| Formulation/Composition 15 | 1 |
| Formulation/Composition 16 | 0 |
| Formulation/Composition 17 | 1 |
| Formulation/Composition 18 | 0 |
| Formulation/Composition 19 | 0 |
| Formulation/Composition 20 | 0 |
| Formulation/Composition 21 | 0 |
| Formulation/Composition 22 | 1 |
| Formulation/Composition 23 | 0 |
| Formulation/Composition 24 | 1 |
| Formulation/Composition 25 | 0 |
| Formulation/Composition 26 | 0 |
| Formulation/Composition 27 | 0 |
| Formulation/Composition 28 | 0 |
| Formulation/Composition 29 | 1 |
| Formulation/Composition 30 | 0 |
| Formulation/Composition 31 | 1 |
| Formulation/Composition 32 | 0 |
| Formulation/Composition 33 | 0 |
| Formulation/Composition 34 | 0 |
| Formulation/Composition 35 | 0 |
| Formulation/Composition 36 | 1 |
| Formulation/Composition 37 | 0 |
| Formulation/Composition 38 | 1 |
| Formulation/Composition 39 | 0 |
| Formulation/Composition 40 | 0 |
| Formulation/Composition 41 | 0 |
| Formulation/Composition 42 | 0 |
| Formulation/Composition 43 | 1 |
| Formulation/Composition 44 | 0 |
| Formulation/Composition 45 | 1 |
| Formulation/Composition 46 | 0 |
| Formulation/Composition 47 | 0 |
| Formulation/Composition 48 | 0 |
| Example 1, WO2000056757A1 | 4 |
| Comparative Formulation/Composition d | 2 |
| Comparative Formulation/Composition e | 3 |
| Comparative Formulation/Composition f | 2 |

Results show that the injection site irritation of the preparations obtained in Formulations of Compositions 1-48 of the present invention is significantly less than that in Example 1 of WO2000056757A1, and stimulation of the preparations obtained in comparative Formulation/Composition d-f is more than that in the Formulations/Compositions of the present invention.

Example 5. Effect of BEA in DSS Induced Mouse Colitis Model

Experimental animals: 72 ICR mice, male and female, 25-29 g body weight before starting the experiment.

Subgrouping: The experimental animals are divided into 6 groups at random, 12 mice in each group: physiological saline group, high dose group (40 mg/kg), moderate dose group (20 mg/kg), low dose group (10 mg/kg) of BEA obtained in Formulation/Composition 1 of the present invention, Dexamethasone (0.1 mg/kg), DSS model group.

Model replication: The experimental mice are injected with 3% DSS and fed with water routinely for 7 days, the colitis model is duplicated.

Administration of drug: the mice are injected with the test drug on the same day when DSS are injected.

Experimental animal management: the general physical condition, loose stools, and bloody stools are observed every day.

The fecal occult blood is tested 3 days after injected with drug. The blood tests are done on day 7. The macrophages are counted and their IL-6 and TNF-alpha are determined. Their inflammation and ulcer level are observed. The colon content is taken to smear, stain and then determined the G+/G−. The thymus, spleen, liver are taken to weight and calculate the organ index. Sections of colon are sent for pathological examination. Results are shown in Table 5-1:

TABLE 5-1

Effect of BEA on Mouse with Colitis induced by DSS

| Group (mg/kg) | Initial weight(g) | Weight before fasting(g) | Final weight (g) | number of animals with bloody stools | number of animals with fecal occult blood (3rd day) | The length of colon(cm) |
|---|---|---|---|---|---|---|
| Control | 27.7 ± 2.3 | 29.4 ± 3.2 | 27.6 ± 2.5 | 0/12 | 0/12 | 12.2 ± 1.2 |
| Model | 27.7 ± 2.0 | 27.7 ± 2.7 | 25.9 ± 2.5 | 10/12 | 8/12 | 8.7 ± 1.0* |
| BEA(10) | 27.9 ± 2.2 | 28.2 ± 2.8 | 26.5 ± 2.6 | 5/12 | 7/12 | 10.4 ± 1.0** |
| BEA(20) | 27.5 ± 1.4 | 27.7 ± 2.5 | 25.7 ± 1.8 | 5/12 | 7/12 | 10.5 ± 0.9** |
| BEA(40) | 27.5 ± 1.4 | 27.6 ± 1.7 | 25.6 ± 1.7 | 6/12 | 6/12 | 9.2 ± 0.8 |
| Dex (0.1) | 28.1 ± 2.2 | 25.3 ± 2.3 | 23.0 ± 2.1*** | 8/12 | 9/12 | 9.9 ± 1.2 |

*$P < 0.01$ vs Control;
**$P < 0.05$ vs Model;
***$P < 0.05$ vs initial weight;
Dex: Dexamethasone;
Control: physiological saline;
Model: DSS fed with water Explanation of the Results:

1. Initial weight represents the animals' weight at the time of subgrouping. There is not significant difference among different groups. All of experimental animals' weight are trending downward except the control group 7 days after the injection with the test drug. The animals' weight reduces in the Dexamethasone group while there is not significant change in animals' weight in BEA group.

2. Fecal occult blood test: Fecal occult blood refers to slight bleeding in the digestive tract, red blood cells are digested and destroyed, and there is not abnormal change of the stool's appearance. Animals with fecal occult blood appear in each group in the third day.

3. Animals with bloody stools: the content of colon is observed carefully during dissection and recorded the visible fresh blood in the content.

4. Length of colon: the colon length of the animals in the model group is apparently shorten compared with that of the control group. DEX and high dose of BEA treatment are effective. The moderate dose is much more effective than low dose.

TABLE 5-2

Effect of BEA on White Blood Cell Count, Abdominal Macrophage Cell Count, IL-6 level and TNF-alpha level in Mice with Colitis Induced by DSS (Mean ± SD, n = 12)

| Group (mg/kg) | White blood cell count (×10$^9$) | Macrophage cell count (×10$^5$) | IL-6 level (pg/ml) | TNFa level (pg/ml) | IL-6/ TNF-alpha |
|---|---|---|---|---|---|
| Control | 3.5 ± 1.2 | 33.0 ± 5.0 | 692.1 ± 273.3 | 72.5 ± 53.9 | 12.7 ± 8.6 |
| Model | 7.5 ± 2.1** | 25.1 ± 6.5 * | 943.3 ± 455.3 | 61.7 ± 53.2 | 16.5 ± 4.5 |
| BEA(10) | 5.9 ± 1.4 | 28.3 ± 8.9 | 551.7 ± 391.4 | 49.5 ± 23.2 | 9.5 ± 7.9 |
| BEA(20) | 5.2 ± 1.5# | 32.3 ± 1.3# | 589.1 ± 227.1 | 49.1 ± 37.0 | 16.8 ± 8.0 |
| BEA(40) | 5.9 ± 2.9 | 24.6 ± 3.4 | 370.8 ± 219.1# | 31.4 ± 15.1 | 12.7 ± 8.6 |
| Dex(0.1) | 5.0 ± 2.6# | 24.4 ± 5.7 | 791.7 ± 234.3 | 92.4 ± 42.1 | 15.8 ± 8.7 |

* $P < 0.05$,
**$P < 0.01$ vs Control,
$P < 0.05$ vs Model

Explanation of the Results:

1. blood cell count: White blood cell count of animals in the model group increased apparently, while the increasing count of white blood cell are reduced significantly in the treated groups, which indicated the test drug is effective for the treatment of inflammation.

2. Macrophage cell count: Abdominal macrophage cell count of animals in the model group decreased apparently but increased significantly in the moderate dose of BEA group, which indicates the test drug is effective for immunodeficiency.

3. Cytokine: Th2 cytokine count is higher in DSS model group. The significant declination of IL-6 level and improvement of IL-6/TNF-alpha level indicates the improvement of immune environment.

TABLE 5-3

Effect of BEA on Immune Organ Weight of ICR Mice with Colitis Induced by DSS (Mean ± SD, n = 12)

| Group (mg/kg) | Thymus (mg) | Thymus index (mg/g) | Spleen (mg) | Spleen index (mg/g) |
|---|---|---|---|---|
| Control | 0.07 ± 0.02 | 2.7 ± 0.7 | 0.11 ± 0.02 | 4.0 ± 0.5 |
| Model | 0.06 ± 0.01 | 2.6 ± 0.5 | 0.18 ± 0.05 | 6.9 ± 1.5** |
| BEA(10) | 0.8 ± 0.01 | 2.7 ± 1.0 | 0.16 ± 0.03 | 5.7 ± 2.0 |
| BEA(20) | 0.8 ± 0.01 | 2.9 ± 0.7 | 0.15 ± 0.03 | 5.9 ± 1.0* |
| BEA(40) | 0.8 ± 0.01 | 3.1 ± 0.7 | 0.16 ± 0.03 | 6.4 ± 1.2 |
| Dex(0.1) | 0.02 ± 0.01** | 0.9 ± 0.4* | 0.18 ± 0.04 | 7.9 ± 1.7 |

**$P < 0.01$ vs Control;
*$P < 0.05$ vs Model

Explanation of the results: Atrophy of thymus and enlargement of spleen indicate inflammatory reaction. Thymus of mice in model group tends to atrophy but not significant. The enlargement of spleen of mice in model group is significant compared with the control group. DEX promotes atrophy of thymus and enlargement of spleen significantly. BEA has no effect on atrophy of thymus while inhibits the enlargement of spleen, which indicates the test drug is effective for the treatment of inflammation.

Further, the animal model for Inflammatory Bowel Diseases (IBD) in the example confirms that BEA may be used to treat MAP-associated diseases, including Crohn's disease (CD), rheumatoid arthritis (RA), Blau syndrome, type 1 diabetes, Hashimoto thyroiditis, multiple sclerosis, Sarcoidosis, and Johne's disease. The example on the effect of BEA in DSS induced mouse colitis model, an IBD model, demonstrates that the BEA aqueous formulation of the present invention is more effective than Dexamethasone, the standard treatment and positive control. Because RA and CD share the same cause and are treated with the same drugs, it's reasonable to predict that a drug that can effectively treat CD by inhibiting MAP, should also be effective against RA. Since BEA is effective in the animal model for CD, it should be effective in treating RA. Therefore, BEA may be used to treat CD and RA.

Example 6. Comparison Dog PK Studies of BEA in Different Formulation

The dog PK of BEA formulations prepared based on literature (Example 1 of WO2000056757A1) and present invention (Formulation of Composition 1 in Example 1) are compared in the experiment.

Nine (9) male Beagle dogs (body weight: 11-13 kg) are divided into 3 groups, 3 dogs per group. The first group is given 5 mg/kg of Formulation of Composition 1, Example 1 of the present invention intramuscularly. The second group is given 5 mg/kg of Example 1 of WO2000056757A1 intramuscularly. The third group is given 5 mg/kg of Example 1 of WO2000056757A1 subcutaneously. Blood is sampled at 0.33, 0.67, 1, 1.5, 2, 4, 6, 8, 16, 24 hours, 2, 3, 4, 5, 6, 7 days. The samples are processed and analyzed by LC-MS/MS to measure the BEA blood concentrations.

As shown in FIG. 1, the results suggest BEA with Formulation of Composition 1, of Example 1 of the present invention has better exposure in blood than BEA with formulation of Example 1 of WO2000056757A1.

Example 7. In-Vitro Effect of BEA Formulations on Macrophage

Line of human macrophages are infected with *M. tuberculosis* reference strain H37Rv, MOI 1 to 5 (5 bacteria per 1 macrophage) and incubated with two different concentrations (5 or 6 M) of 7OH-DHEA, natural DHEA, BEA with Example 1 of WO2000056757A1 formulation (F1) and BEA with Formulation of Composition 1 in Example 1 Invention formulation (F2), and Curcumin.

Figure 2A:
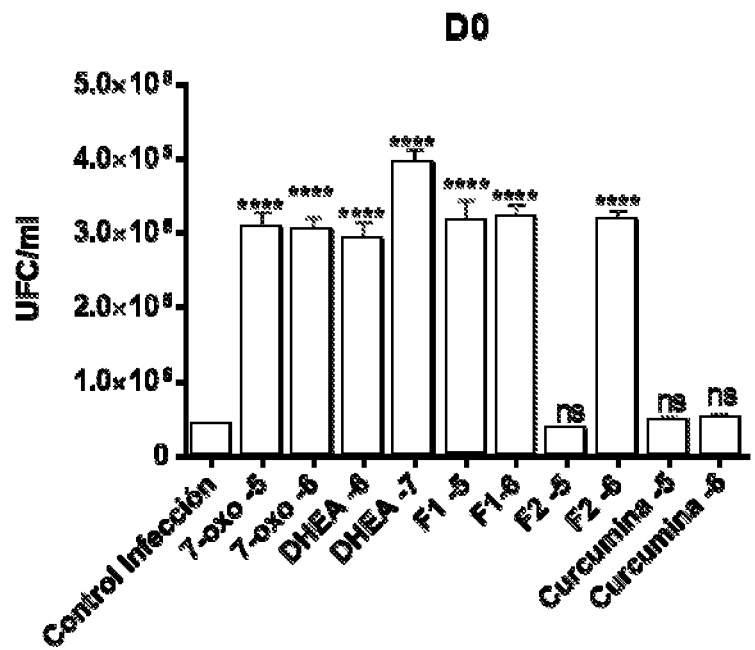
FIG. 2(a) shows numbers of intracelllular live bacilli in the macrophages that are incubated at various compositions at day 0, that is, the starting counts.
Figure 2B:
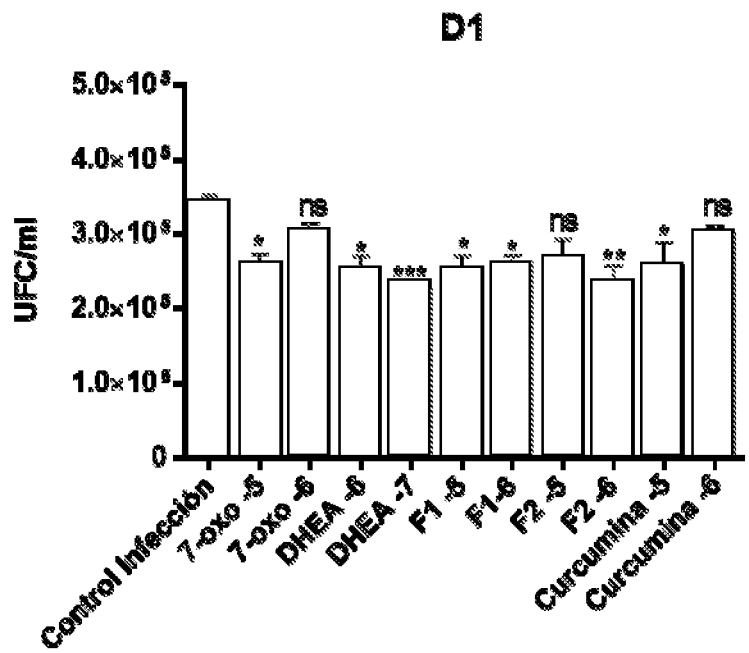
FIG. 2(b) shows numbers of intracelllular live bacilli in the macrophages that are incubated at various compositions at day 1, that is, after 24 hours of incubation.
Figure 2C:
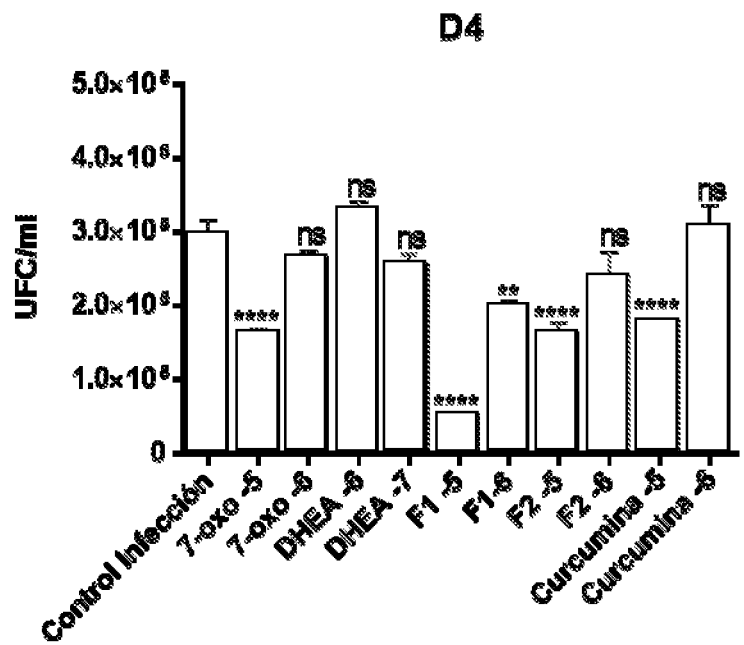
FIG. 2(c) shows numbers of intracelllular live bacilli in the macrophages that are incubated at various compositions at day 4, that is, after 4 days of incubation, all data are in Example 7 of the present invention.

After 1 hr (DO), 24 hr (1 D) and 4 days (4D), extracellular bacteria are washed away and macrophages are lysed and plated in order to determine the number of intracellular live bacilli, DO indicates the phagocytic activity and is used to compare with the control that corresponds to infected macrophages incubated without any compound, all the DHEA derivatives are quite efficient except F2 at 5M concentration. After 1 and 4 days, macrophages kill bacilli, so there is a decrease in live bacilli produced by DHEA derivatives being highly significant at day 4 by F1 at 5M concentration, followed by F2 at 5M. The results are shown in FIGS. 2(*a*), 2(*b*), and 2(*c*). (*$p<0.05$;  $p<0.01$; * $p<0.005$ when compared to the control).

Example 8. Effect of BEA Present Invention Formulations in Mouse Mycobacteria Tuberculosis Model Non-aqueous BEA formulation has been reported to have anti-Mycobacteria Tuberculosis in a mouse model (Hernandez-Pando, R., et al. (2005)). The objective of this study is to prove that the invention formulation of BEA is as effective as the existing non-aqueous BEA formulation in a parallel study. The positive results confirm that the invention formulation will likely to be effective in all the indications demonstrated by the existing formulation, for example, HIV, malaria and Mycobacteria tuberculosis.

In this experiment, F1 is a BEA formulation prepared based on literature (Example 1 of WO2000056757A1). F2 is a BEA formulation prepared based present invention (Formulation of Composition 1 in Example 1).

Male BALB/c mice are infected intratracheally with *M. tuberculosis* strain H37Rv and after 2 months groups of 8 animals are treated by subcutaneous (SC) or intratracheal (IT) routes with F1 (BEA with Example 1 of WO2000056757A1 formulation) or F2 (BEA with Formulation of Composition 1 of invention formulation in Example 1) each other day, groups of 4 animals are euthanized after 1 and 2 months, right lungs are homogenized and plated in solid growth medium 7H9, the number of colonies are counted after 21 days, left lung is perfused with formalin. Both formulations have good effect and significantly reduced the colony-forming units (CFUs) compared with control. 2 month of treatment is better than 1 month. The CFUs for the experiments using F1 or F2 are similar. F2 is slightly better after 2 months of administration by intratracheal route. These results proved that the aqueous invention formulation of BEA is equally or more effective than the existing formulations.

TABLE 8-1

Effect of BEA Formulations in Mouse MT Model

| Drug | CFU | |
|---|---|---|
| | 1 Month | 2 Month |
| Control | 14.3 | 10.9 |
| F1-IT | 5.7 | 4.6 |
| F2-IT | 4.9 | 2.8 |
| F1-SC | 4.2 | 12.3 |
| F2-SC | 6.0 | 4.2 |

Example 9. Effect of BEA Invention Formulation in Mouse Asthma Model

Asthma is due to chronic inflammatory disease and has been linked to *Chlamydia pneumoniae* (Black, P. et al, Eur. Respir. J., 15(2), 254-9 (2000)). Given BEA's anti-inflammatory effect, it's predicted that BEA should be effective in treating asthma. This experiment is designed to demonstrate BEA's efficacy with a mouse asthma model.

In this experiment, the BEA formulation is prepared based present invention formulation (Formulation of Composition 1 in Example 1).

18 BALB/c male mice, 8 weeks old are sensitized with two intraperitoneal (IP)administrations, 5 days apart, of 10 μg chicken egg ovalbumin (OVA, grade V; Sigma) emulsified in 1 mg of aluminum hydroxide (Thermo Scientific, Rockford, Ill., USA) in a total volume of 100 μl. Then, after one month mice are challenged via intratracheal (IT) administration of 0.75% OVA. BEA formulation is administered at 0.2 mg/kg dose in an injection volume of 0.1 mL in two different routes of administration (intratracheal and subcutaneous (SC)), one hour after the OVA challenge and one dose per day for up to 7 days. Then, animals are euthanized by exsanguination under pentobarbital anesthesia. The bronchioalveolar lavage (BAL) of the mice are used to determine the total counts of inflammatory cells. Control mice receive saline solution intraperitoneally (IP). All experiments are performed in accordance with INCMN Mexico City regulations. Two independent experiments are performed.

Table 9-1 summarized the results of the total number of inflammatory cells in bronchioalveolar lavage after 3 and 7 days of BEA formulation treatment compared with control. The mice receiving BEA formulation both intratracheally and subcutaneously have significantly less inflammatory cell counts compared with the mice receiving saline, a reduction of 67% and 71% respectively, at Day 3. 74% and 55% reduction in inflammatory cell counts are achieved at Day 7. These results indicate that the BEA formulation is effective in treating asthma. They also support the prediction that BEA formulation can be effective in treating other *Chlamydia pneumoniae* related chronical diseases.

TABLE 9-1

Total Number of Inflammatory Cells in
Bronchioalveolar Lavage after Treatment

| Drug | Inflammatory Cell Number | |
|---|---|---|
| | Day 3 | Day 7 |
| BEA (IT) | $4.61 \times 10^4$ | $5.99 \times 10^4$ |
| BEA (SC) | $4.07 \times 10^4$ | $1.06 \times 10^5$ |
| Saline (IT) | $1.38 \times 10^5$ | $2.36 \times 10^5$ |

Example 10. The Effect of BEA Formulation on Mouse Metabolic Syndrome

In this experiment, F1 is a BEA formulation prepared based on literature (Example 1 of WO2000056757A1). F2 is a BEA formulation prepared based present invention (Formulation of Composition 1 in Example 1).

This experiment is designed based on a mouse metabolic syndrome model reported by Ana Maria Leal-Diaz, M. et al., "Aguamiel concentrate from Agave salmiana and its extracted saponins attenuated obesity and hepatic steatosis and increased Akkermansia muciniphila in C57BL6 mice," Sci. Rep., Nature, 6, 34242 (2016).

Young BALB/c mice (3 weeks of age) are fed with hypocaloric diet. At 8 weeks of age, they received one dose of Estreptozotocin (100 mg) via IP route. 8 weeks later, the mice are administered with BEA formulations, F1 and F2, via IT, SC, and IT+SC respectively, at 0.2 mg/kg, 3 times per week for 8 weeks. IT+SC group receives twice of the dose.

Oral glucose tolerance test (OGTT) is conducted at the end of 8 weeks of BEA formulation treatment by administering 100 µl of 8% glucose solution per mice by gavage after 4 hours of fasting. Blood samples are collected from the tail vein at 0, 15, 30, 60, and 120 min after glucose administration. The AUC is calculated using the trapezoid rule. The normal blood glucose level is measured at the same time period.

Figure 4A:
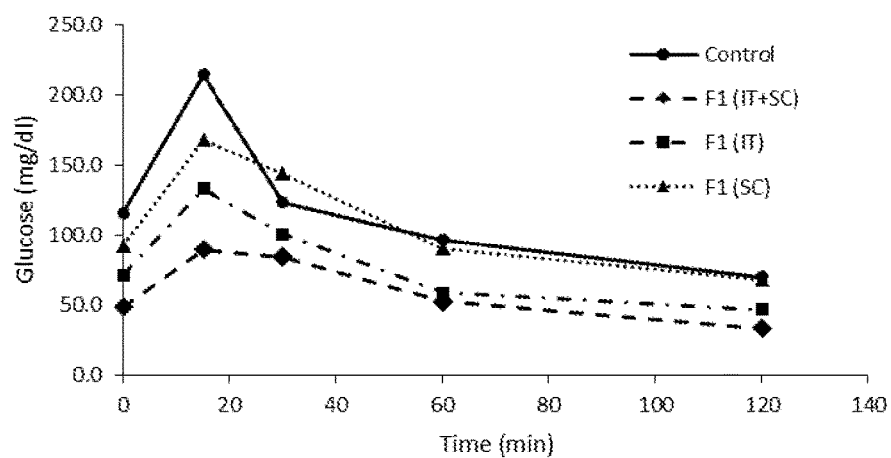
Figure 4B:
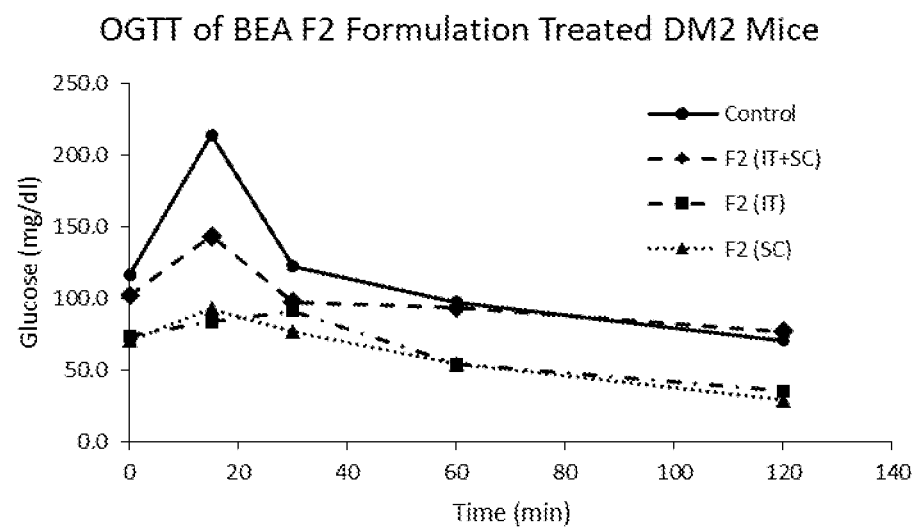
Figure 4C:
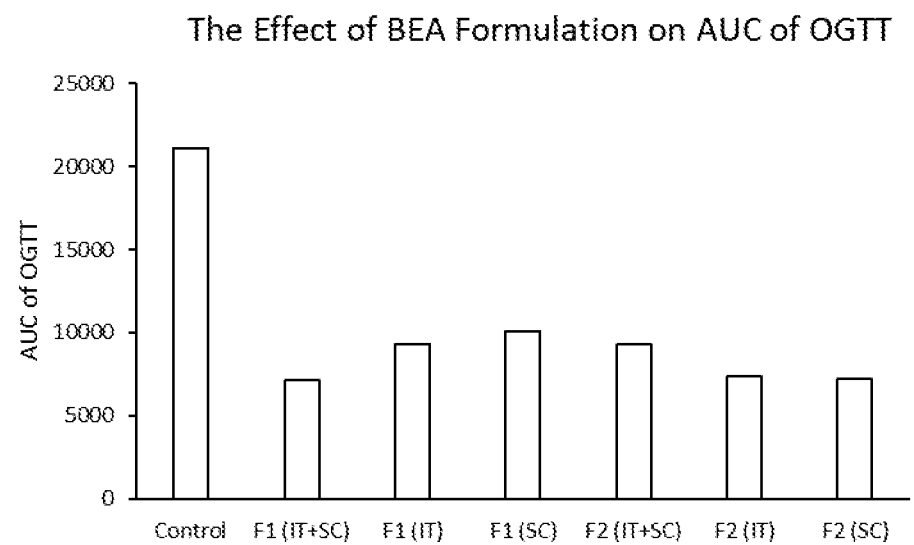

FIG. 4(a) is the OGTT results for Estreptozotocin induced type-2 diabetes mellitus (DM2) mice treated with F1 formulation. FIG. 4(b) is the OGTT results for Estreptozotocin induced type-2 diabetes mellitus (DM2) mice treated with F2 formulation. FIG. 4(c) is the AUC (area under the curve) of blood glucose of OGTT.

The OGTT results showed that both F1 and F2 formulations through both IT and SC routs can effectively enhance the glucose tolerance level of DM2 mice. The AUC data also suggest that F2, a BEA formulation prepared based present invention (Formulation of Composition 1 in Example 1) is superior to F1, a BEA formulation prepared based on literature (Example 1 of WO2000056757A1).

Figure 4D:
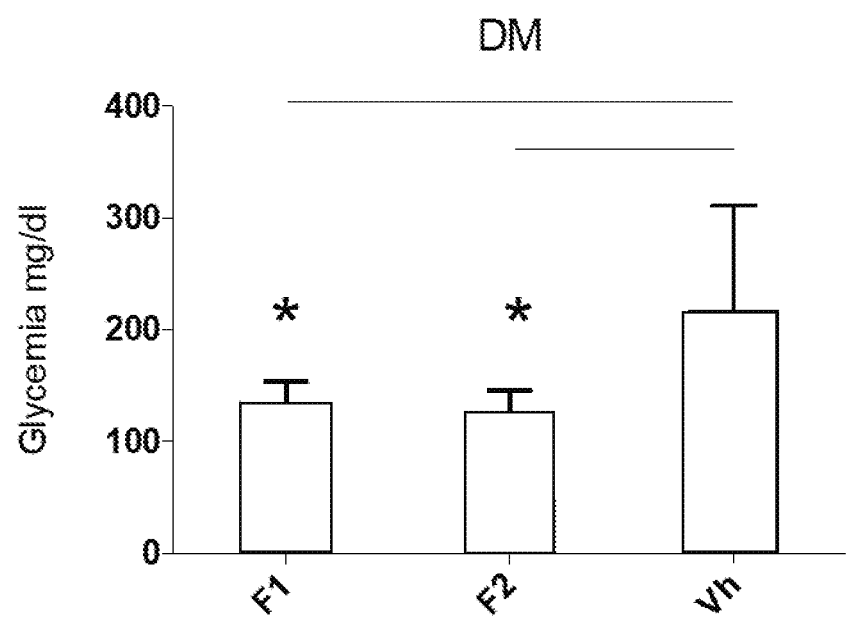

FIG. 4(d) is the normal glucose levels of DM2 mice treated with F1 and F2 compared with treated with vehicle. The results indicate that BEA, in both F1 and F2 formulations can normalize the blood glucose level of DM2 mice. Overall, the results of this experiment suggest that BEA with present invention formulation is a good candidate for treating type 2 diabetes.

Example 11. Evaluation of BEA Anti-Myeloma Activity in Vk*MYC Mice

The experiments are conducted by Dr. Marta Chesi's group at Comprehensive Cancer Center, Mayo Clinic, Scottsdale, Ariz. The experimental details are described in her publication (Chesi, M. et al., 2012, Drug response in a genetically engineered mouse model of multiple myeloma is predictive of clinical efficacy, Blood, 120(2), 376-385). 3 Vk*MYC Mice are evaluated. Mice M5645B and M5489D are dosed 15 and 20 mg/kg/day BEA formulation on day 1-5, 8-12 through I.P. route of administration. The M-Spike value are assessed at day 7 and 14 respectively. Mouse M5369 is dosed 15 mg/kg/day BEA formulation on day 1-5, 8-12 through I.M. route of administration, then 15 mg/kg/day on day 15-19 through I.P. route of administration. The M-Spike value are assessed at day 7, 14 and 21 respectively.

Figure 3:
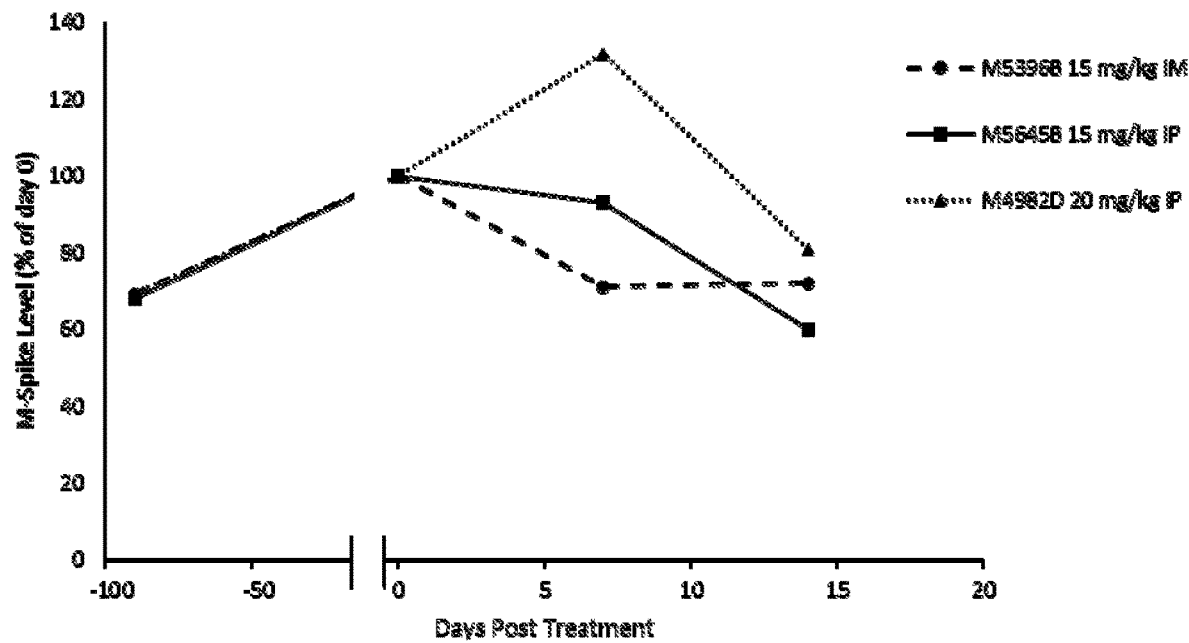
FIG. 3 shows the change of M-spike values over time in mice M5396B, M5645B, and M4982D in Example 11 of the present invention.

Results as shown in FIG. 3 indicates that 40% reduction of M-Spike in the in vivo model is achieved at 15 mg/kg/day in Vk*MYC Mice, strongly suggesting the BEA formulation is active against multiple myeloma. As BEA's anti-multiple myeloma activities are shown in the Example, it further supports that BEA may be used as a cancer immunotherapy agent.

I claim:

1. A composition, comprising
at least 30% w/w water based on total weight of the composition, and
a compound of Formula I,

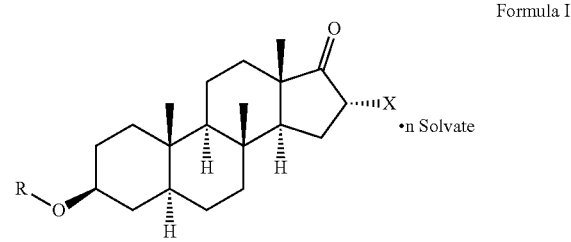

Formula I wherein n is 0 to 4;
the solvate is $H_2O$, $C_{1-4}$—OH, $C_{1-4}$—OH, $C_{1-4}$—COON, $C_{1-4}$—COOC$_{1-4}$ tetrahydrofuran, 1,4-dioxane, $(CH_3)_2O$, $(C_2H_5)_2O$, $HC(O)N(CH_3)_2$, $(CH_3)_2SO$, or a combination thereof;
X is F, Cl, Br, or I;
R is —H or a trialkyl silyl group —Si-(alkyl)$_3$, and each of the three alkyls in the trialkyl silyl group is independently selected from the group consisting of a methyl, an ethyl, a propyl, a butyl, a pentyl, and a hexyl,
wherein the compound is in form of particles stabilized as an aqueous suspension in the water.

2. A water dispersible dry composition according to claim 1, wherein the water dispersible dry composition is prepared by freeze-drying the composition of claim 1.

3. The water dispersible dry composition of claim 2, wherein the water dispersible dry composition is a lyophilized formulation comprising the compound, a surfactant, a suspending agent, and at least one lyophilization protectant, and amount of the compound is at 3 mg to 500 mg, a ratio of the compound to the surfactant is 1:50-500:1, and a ratio of the compound to the suspending agent is 0.1:10-500:1.

4. A reconstituted composition, comprising
the water dispersible dry composition of claim 2, and a diluent,
wherein the diluent comprises water, and content of the water in the reconstituted composition is at least 30% w/w of the reconstituted composition.

5. A method for making the water dispersible dry composition of claim 2, comprising
preparing the composition comprising the compound of Formula I in form of particles stabilized in an aqueous suspension and water of at least 30% w/w of the composition,
freeze-drying the composition to obtain the water dispersible dry composition of claim 2.

6. A method for using the water dispersible dry composition of claim 2, comprising
mixing the water dispersible dry composition with a diluent to form a reconstituted composition, and
administering to a subject in need of a treatment a therapeutically effective amount of the reconstituted composition.

7. The composition of claim 1, wherein the size of the particles is in a range of 0.01 µm to 15 µm.

8. The composition of claim 1, further comprising a surfactant, a suspending agent, and a pharmaceutical excipient.

9. The composition of claim 8, wherein the surfactant is a poloxamer, polysorbate, polyoxyethylated castor oil polyoxyethylene hydrogenated castor oil, polyethylene glycol (PEG)-8-octylic acid/decanoic acid and polyethylene glycol (PEG) hydroxy stearic acid ester, egg yolk lecithin, soybean lecithin, sodium oleate, bile salt, or a mixture thereof.

10. The composition of claim 8, wherein the suspending agent is cellulose derivatives such as methylcellulose, hydroxyethylcellulose, carboxymethylcellulose, sodium carboxymethylcellulose, microcrystalline cellulose), polyethylene glycol (PEG), polyvinylpyrrolidone (PVP), gelatin, alginates, acacia, tragacanth, xanthan gum, bentonite, carbomer, carrageenan, or a mixture thereof.

11. The composition of claim 8, wherein the pharmaceutical excipient is water for injection, a pH regulator, an osmotic pressure regulator, a freeze-drying protective additive, a sequestering agent, an antioxidant, a preservative, a medicinal ingredient, or a mixture thereof.

12. The composition of claim 11, wherein the pharmaceutical excipient comprises a preservative, and the preservative is methanol, ethanol, n-propanol, isopropanol, n-butanol, 2-butanol, t-butanol, Vitamin C, sodium bisulfite, sodium thiosulfate, sodium metabisulfite, L-cysteine, an amino acid, or a combination thereof.

13. The composition of claim 8, wherein the composition is an injectable suspension comprising
0.3-25% (w/v) of the compound,
0.01-5% (w/v) of the surfactant,
0.01-3% (w/v) of the suspending agent, and
an osmotic pressure regulator as the pharmaceutical excipient.

14. The composition of claim 13, wherein the osmotic pressure regulator is sodium chloride or dextrose.

15. The composition of claim 1, wherein the solvate is water, R is a hydrogen, X is a bromine, n is 0.5, and the compound is 16alpha-bromo-3beta-hydroxy-5alpha-androstan-17-ketone hemihydrate having a structure:

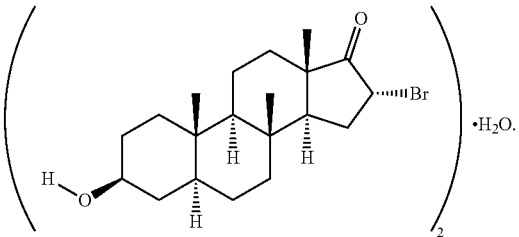

16. The composition of claim 1, wherein 90% of the particles are less than 15 µm in size.

* * * * *

UNITED STATES PATENT AND TRADEMARK OFFICE
CERTIFICATE OF CORRECTION

PATENT NO. : 10,836,788 B2
APPLICATION NO. : 16/267815
DATED : November 17, 2020
INVENTOR(S) : Yu Ge Page 1 of 3

It is certified that error appears in the above-identified patent and that said Letters Patent is hereby corrected as shown below:

On the Title Page

Right column, (57) Abstract, the structure of the compound of formula I shall be changed from:

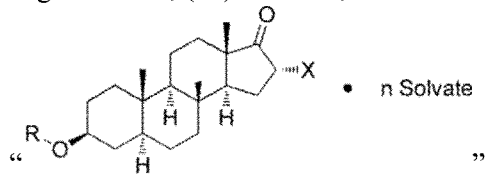

"

To:

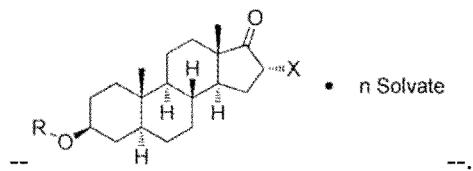

--.

In the Specification

Column 1, Lines 30-39, the structure of the compound of BEA shall be changed from:

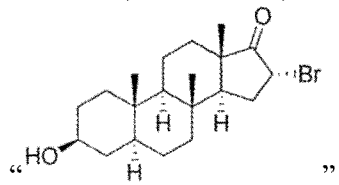

"

To:

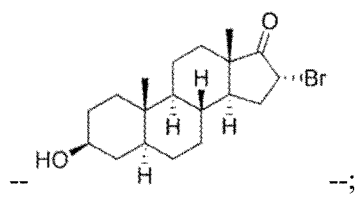

--;

Signed and Sealed this
Twenty-fifth Day of October, 2022

*Katherine Kelly Vidal*

Katherine Kelly Vidal
*Director of the United States Patent and Trademark Office*

Column 9, Lines 56-65, the structure of the compound of formula I change from:
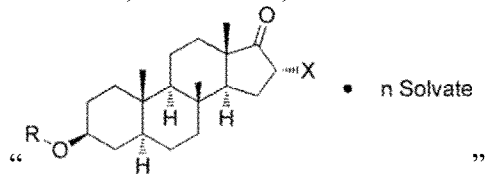
" "
To:
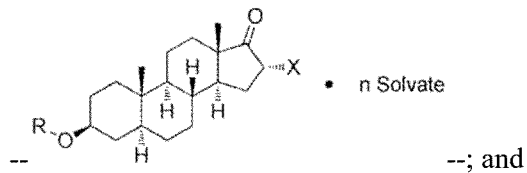
-- --; and
Column 11, Lines 20-29, the structure of the hemihydrate compound shall be changed from:
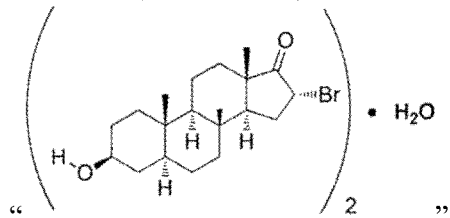
" "
To:
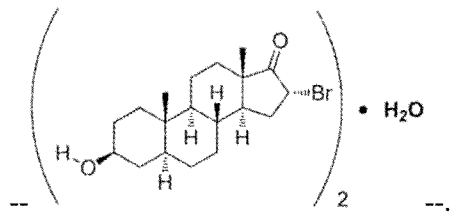
-- --.
In the Claims
Column 56, Lines 27-36, in Claim 1, the structure of the compound of formula I change from:
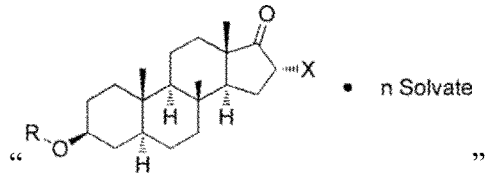
" "
To:
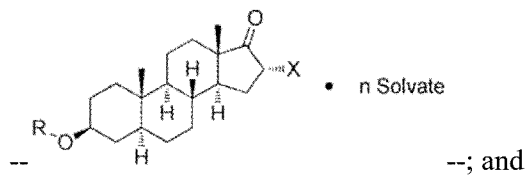
-- --; and

CERTIFICATE OF CORRECTION (continued)
U.S. Pat. No. 10,836,788 B2

Column 58, Lines 22-31, in Claim 15, the structure of the hemihydrate compound shall be changed from:

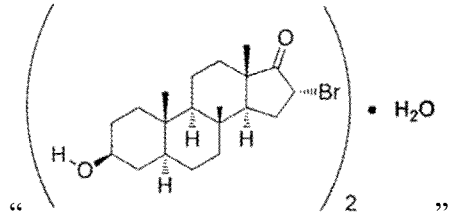

" "

To:

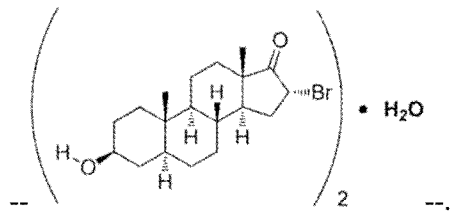

-- --.